US007935682B2

(12) United States Patent
Gomer et al.

(10) Patent No.: US 7,935,682 B2
(45) Date of Patent: May 3, 2011

(54) WOUND HEALING DRESSING FOR ENHANCING FIBROCYTE FORMATION

(75) Inventors: Richard Gomer, Houston, TX (US); Darrell Pilling, Pearland, TX (US)

(73) Assignee: William Marsh Rice University, Houston, TX (US)

( * ) Notice: Subject to any disclaimer, the term of this patent is extended or adjusted under 35 U.S.C. 154(b) by 738 days.

(21) Appl. No.: 11/158,723

(22) Filed: Jun. 22, 2005

(65) Prior Publication Data

US 2006/0002938 A1 Jan. 5, 2006

Related U.S. Application Data

(63) Continuation-in-part of application No. PCT/US2003/041183, filed on Dec. 22, 2003.

(60) Provisional application No. 60/436,046, filed on Dec. 23, 2002, provisional application No. 60/436,027, filed on Dec. 23, 2002, provisional application No. 60/515,776, filed on Oct. 30, 2003, provisional application No. 60/519,467, filed on Nov. 12, 2003, provisional application No. 60/525,175, filed on Nov. 26, 2003.

(51) Int. Cl.
| | |
|---|---|
| A61K 31/715 | (2006.01) |
| A61K 31/729 | (2006.01) |
| A61K 38/18 | (2006.01) |
| A61K 45/00 | (2006.01) |
| A61K 9/14 | (2006.01) |
| A61K 9/16 | (2006.01) |

(52) U.S. Cl. ......... 514/54; 424/85.2; 424/484; 424/488; 424/491

(58) Field of Classification Search .................. None
See application file for complete search history.

(56) References Cited

U.S. PATENT DOCUMENTS

| | | | | |
|---|---|---|---|---|
| 4,233,969 | A | 11/1980 | Lock et al. | 128/156 |
| 4,556,056 | A | 12/1985 | Fischer et al. | 128/156 |
| 4,782,014 | A | 11/1988 | Serban et al. | 435/7 |
| 5,092,876 | A | 3/1992 | Dhawan et al. | 623/11 |
| 5,591,709 | A * | 1/1997 | Lindenbaum | 514/4 |
| 5,654,186 | A | 8/1997 | Cerami et al. | 435/325 |
| 5,698,589 | A | 12/1997 | Allen | 514/509 |
| 5,804,446 | A | 9/1998 | Cerami et al. | 435/385 |
| 5,846,796 | A | 12/1998 | Cerami et al. | 435/172.3 |
| 6,037,458 | A | 3/2000 | Hirai et al. | 530/415 |
| 6,054,121 | A | 4/2000 | Cerami et al. | 424/93.7 |
| 6,126,918 | A | 10/2000 | Pepys et al. | 424/9.1 |
| 6,174,526 | B1 | 1/2001 | Cerami et al. | 424/93.1 |
| 6,365,570 | B1 | 4/2002 | Van Kessel et al. | 514/8 |
| 6,406,698 | B1 | 6/2002 | Svehang et al. | 424/184.1 |
| 6,537,811 | B1 | 3/2003 | Freier | 435/375 |
| 6,600,019 | B2 | 7/2003 | Prayaga et al. | 530/350 |
| 6,872,541 | B2 | 3/2005 | Mills | 435/7.21 |
| 2002/0058284 | A1 | 5/2002 | Winkel | 435/7.1 |
| 2003/0003567 | A1 | 1/2003 | Barber et al. | 435/235.1 |
| 2003/0022245 | A1 | 1/2003 | Mills | 435/7.8 |
| 2004/0068095 | A1 | 4/2004 | Shimkets et al. | 530/350 |
| 2005/0238620 | A1 | 10/2005 | Gomer et al. | 424/85.2 |

FOREIGN PATENT DOCUMENTS

| | | |
|---|---|---|
| DE | 28 49 570 | 6/1980 |
| EP | 1 090 630 | 4/2001 |
| JP | 54-5023 | 1/1979 |
| JP | 11-319542 | 11/1999 |
| WO | 9941285 | 8/1999 |
| WO | 99/45900 | 9/1999 |
| WO | 0174300 A1 | 10/2001 |
| WO | 03031572 | 4/2003 |
| WO | 03097104 | 11/2003 |
| WO | 2004016750 | 2/2004 |
| WO | 2004058292 | 7/2004 |
| WO | 2004059318 | 7/2004 |
| WO | 2005110474 | 11/2005 |
| WO | 2005115452 | 12/2005 |
| WO | 2006002438 | 1/2006 |

OTHER PUBLICATIONS

Oriente A, et al. Interleukin-13 modulates collagen homeostasis in human skin and keloid fibroblasts. J. Pharm. Exp. Therap. 2000. vol. 292, No. 3, pp. 988-994.*
Lindenbaum ES, et al. Serum-free cell culture medium induces acceleration of wound healing in guinea-pigs. Burns. 1995, vol. 21, No. 2, pp. 110-115.*
F.C. de Beer et al., "Fibronectin and C4-Binding Protein are Selectively Bound by Aggregated Amyloid Component", The Rockefeller University Press, vol. 154, pp. 1134-1149, Oct. 1981.
Lawrence A. Potempa et al., "Effect of Divalent Metal Ions and pH Upon the Binding Reactivity of Human Serum Amyloid P Component, a C-Reactive Protein Homologue, for Zymosan", The Journal of Biological Chemistry, vol. 260, pp. 12142-12147, Oct. 5, 1985.
Terry W. Du Clos, "C-Reactive Protein Reacts With the U1 Small Nuclear Ribonucleoprotein", The Journal of Immunology, vol. 143, pp. 2553-2559, Oct. 15, 1989.
Marilyn R. Brown et al., "Receptor-Ligand Interactions Between Serum Amyloid P Component and Model Soluble Immune Complexes", The Journal of Immunology, vol. 151, pp. 2087-2095, Aug. 15, 1993.

(Continued)

*Primary Examiner* — Robert Landsman
*Assistant Examiner* — Bruce D Hissong
(74) *Attorney, Agent, or Firm* — Baker Botts L.L.P.

(57) ABSTRACT

The present invention relates to the ability of SAP to suppress the differentiation of monocytes into fibrocytes. It also relates to the ability of IL-4 and IL-3 to enhance the differentiation of monocytes into fibrocytes. Methods and compositions for binding SAP, decreasing SAP levels and suppressing SAP activity are provided. Methods of using, inter alia, CPHPC, the 4,6-pyruvate acetyl of beta-D-galactopyranose, ethanolamines, high EEO agarose, IL-4, and IL-13, and anti-SAP antibodies and fragments thereof to increase monocyte differentiation into fibrocytes are provided. These methods are useful in a variety of applications, including wound healing. Wound dressings are also provided. Finally, the invention may include assays for detecting the ability of various agents to modulate monocyte differentiation into fibrocytes and to detect monocyte defects.

23 Claims, 16 Drawing Sheets
(5 of 16 Drawing Sheet(s) Filed in Color)

OTHER PUBLICATIONS

Lorraine L. Marnell et al., "C- Reactive Protein Binds to FcγR1 in Transfected COS Cells", The American Association of Immunologists, 9 Pgs, Feb. 22, 1995.

Annalisa D'Andrea et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production", The Rockefeller University Press, vol. 181, pp. 537-546, Feb. 1995.

Kamyar Zahedi, "Characterization of the Binding of Serum Amyloid P to Type IV Collagen", The Journal of Biological Chemistry, vol. 271, No. 25, pp. 14897-14902, Jun. 21, 1996.

Marc Daëron, "Fc Receptor Biology", www.arjournals.annualreviews.org, pp. 203-234, 1997.

Kamyar Zahedi, "Characterization of the Binding of Serum Amyloid P to Laminin", The Journal of Biological Chemistry, vol. 272, No. 4, pp. 2143-2148, Jan. 24, 1997.

Carla J.C. de Haas et al., "A Synthetic Lipopolysaccharide-Binding Peptide Based on Amino Acids 27-39 of Serum Amyloid P Component Inhibits Lipopolysaccharide-Induced Responses in Human Blood", The Journal of Immunology, pp. 3607-3615, 1998.

Dwaipayan Bharadwaj et al., "The Major Receptor for C-Reactive Protein on Leukocytes Is Fcγ Receptor II", The Journal of Experimental Medicine, vol. 190 No. 4, pp. 585-590, Aug. 16, 1999.

M.C.M. Bickerstaff et al., "Serum Amyloid P Component Controls Chromatin Degration and Prevents Antinuclear Autoimmunity", Nature Medicine, vol. 5, No. 6, pp. 694-697, Jun. 1999.

Fayyaz S. Sutterwala et al., "The Taming of IL-12 Suppressing the production of Proinflammatory Cytokines", Journal of Leukocyte Biology, vol. 65, pp. 543-551, May 1999.

Richard F. Mortensen et al., "Regulation of Phagocytic Leukocyte Activities by C-reactive Protein", Journal of Leukocyte Biology, vol. 67, pp. 495-500, Apr. 2000.

Mary-Pat Stein et al., "C-reactive Protein Binding to FcγRIIa on Human Monocytes and Neutrophils is Allele-Specific", The Journal of Clinical Investigation, vol. 105, pp. 369-376, Feb. 2000.

Dwaipayan Bharadwaj et al., "Serum Amyloid P Component Binds to Fcγ Receptors and Opsonizes Particles for Phagocytosis", The Journal of Immunology, vol. 166, pp. 6735-6741, 2001.

Eirikur Saeland et al., "Human C-reactive Protein Does not Bind to FcγRIIa on Phagocytic Cells", The Journal of Clinical Investigation, vol. 107 No. 5, pp. 641-643, Mar. 2001.

Carolyn Mold et al., "Serum Amyloid P Component and C-Reactive Protein Mediate Phagocytosis Through Murine FcγRs", The Journal of Immunology, vol. 166, pp. 1200-1205, 2001.

Katherine B. Bodman-Smith et al., "C-Reactive Protein-Mediated Phagocytosis and Phospholipase D Signalling Through the High-Affinity Receptor for Immunoglobulin G (FcγRI)", The Journal of Immunology, vol. 107 No. 2, pp. 252-260, Oct. 2002.

Matthias Schmidt et al., "Identification of Circulating Fibrocytes as Precursors of Bronchial Myofibroblasts in Asthma", The Journal of Immunology, vol. 170, pp. 380-389, Apr. 22, 2003.

Liju Yang et al., "Peripheral Blood Fibrocytes From Burn Patients: Identification and Quantification of Fibrocytes in Adherent Cells Cultured From Peripheral Blood Mononuclear Cells", Laboratory Investigation, vol. 82, No. 9, pp. 1183-1192, Apr. 15, 2002.

Thomas A. Wynn, "IL-13 Effector Functions", www.arjournals.annualreviews.org, pp. 425-456, 2003.

Roderick J. Philips et al., "Circulating Fibrocytes Traffic to the Lungs in Response to CXCL 12 and Mediate Fibrosis", The Journal of Clinical Investigation, vol. 114, No. 3, pp. 438-446, Aug. 2004.

Bethany B. Moore et al., "CCR2-Mediated Recruitment of Fibrocytes to the Alveolar Space After Fibrotic Injury", American journal of Pathology, vol. 166, No. 3, pp. 675-684, Mar. 2005.

Luca Mori et al., "Fibrocytes Contribute to the Myofibroblast Population in Wounded Skin and Originate From the Bone Marrow", www.sciencedirect.com, pp. 81-90, Aug. 10, 2004.

Liju Yang, PhD et al., "Identification of Fibrocytes in Postburn Hypertrophic Scar", Wound Repair and Regeneration, vol. 13, No. 4, pp. 398-404, Jan. 17, 2005.

Riichiro Abe et al., "Peripheral Blood Fibrocytes: Differentaion Pathway and Migration to Wound Sites", The Journal of Immunology, vol. 166, pp. 7556-7562, 2001.

Jason Chesney et al., "The Peripheral Blood Fibrocyte is a Potent Antigen-Presenting Cell Capable of Priming Naive T Cells in Situ", Journal of Immunology, vol. 94, pp. 6307-6312, Jun. 1997.

Darrell Pilling et al., "Inhibition of Fibrocyte Differentiation by Serum Amyloid P1", The Journal of Immunology, vol. 171, pp. 5537-5546, 2003.

C.N. Metz, "Fibrocytes: A unique Cell Population Implicated in Wound Healing", Cell. Mol. Life Sci., vol. 60, pp. 1342-1350, Jan. 16, 2003.

R. Bucala et al., "Circulating Fibrocytes Define a New Leukocyte Subpopulation That Mediates Tissue Repair", Molecular Medicine, vol. 1, No. 1, pp. 71-81, Nov. 1994.

J. Chesney et al., "Peripheral Blood Fibrocytes: Mesenchymal Precursor Cells and the Pathogenesis of Fibrosis", Curr.Rheumatol.Rep 2:501-505, 2000.

J. Chesney et al., "Regulated Production of Type I Collagen and Inflammatory Cytokins by Peripheral Blood Fibrocytes", The Journal of Immunology, pp. 15, 1998.

M. Chi et al., "C-Reactive Protein Induces Signaling Through FcγRIIa on HL-60 Granulocytes", The Journal of Immunology, pp. 1413-1418, 2002.

R.B. Christner et al., "Binding of Human Serum Amyloid P-Component to Phosphocholine", Archives of Biochemistry and Biophysics, vol. 314, No. 2, pp. 337-343, Nov. 1, 1994.

Richard A.F. Clark, "Fibrin and Wound Healing", Annals New York Academy of Sciences 936, pp. 355-367, 2001.

Marc Daëron, "Structural Bases of FcγR Functions", Int.Rev.Immunol. 16:1-27, 1997.

F.C. De Beer et al., "Isolation of Human C-Reactive Protein and serum Amyloid P Component", Journal of Immunological Methods, pp. 17-31, 1982.

E. Saeland et al., "Human C-Reactive Protein Does not Bind to FcγRIIa on Phagocytic Cells", The Journal of Clinical Investigation, vol. 107, No. 5, pp. 641-643, Mar. 2001.

H. Gewurz et al., "Structure and Function of the Pentraxins", Current Opinion in Immunology, vol. 7, pp. 54-64, 1995.

M.G. Cappiello et al., "Suppression of IL-12 Transcription in Macrophages Following Fcγ Receptor Ligation", The Journal of Immunology, vol. 166, pp. 4498-4506, 2001.

Ingo Hartlapp et al., "Fibrocytes Induce an Angiogenic Phenotype in Cultured Endothelial Cells and Promote Angiogenesis in Vivo", The FASEB Journal, vol. 15, pp. 2215-2224, Oct. 2001.

Niels H.H. Heegaard et al., "Ligand-Binding Sites in Human Serum Amyloid P Component", Eur.J.Biochem. 239:850-856, 1996.

Charles R.K. Hind et al., "Human Serum Amyloid P Component, a Circulating Lectin with Specificity for the Cyclic 4,6-Pyruvate Acetal of Galactose: Interaction with Varous Bacteria", Biochem.J. 225:107-111, 1985.

Winston L. Hutchinson et al., "Human Serum Amyloid P Component is a Single Uncomplexed Pentamer in Whole Serum", Molecular Medicine, vol. 6, No. 6, pp. 482-493, 2000.

Guido Majno, "Chronic Inflammation: Links With Angiogenesis and Wound Healing", American Journal of Pathology, vol. 153, No. 4, pp. 1035-1039, Oct. 1998.

M.B. Pepys et al., "Serum Amyloid P Component is the Major Calcium-Dependent Specific DNA Binding Protein of Serum", Biochemical and Biophysical Research Communications, vol. 148, No. 1, pp. 208-313, Oct. 14, 1987.

M.B. Pepys et al., "Amyloid P Component. ACritical Review", Amyloid: Int. J. Exp. Invest., vol. 4, pp. 274-295, 1997.

Diana M. Steel et al., "The Major Acute Phase Reactants: C-Reactive Protein, Serum Amyloid P Component and Serum Amyloid A Protein", Immunology Today, vol. 15, No. 2, pp. 81-88, 1994.

Giorgio Trinchieri, "Interleukin-12 and the Regulation of Innate Resistance and Adaptive Immunity", Nature Reviews Immunology, vol. 3, pp. 133-146, Feb. 2003.

John E. Volanakis, "Human C-Reactive Protein: Expression, Structure, and Function", Molecular Immunology, vol. 28, pp. 189-197, 2001.

International Search Report for European Patent Application No. 03 800 146.7 (5 pages), Sep. 22, 2006.

Ashcroft et al., "Simple Method of Estimating Severity of Pulmonary Fibrosis on a Numerical Scale", J Clin Pathol 41, pp. 467-470, 1988.

Ashikawa et al., "Piceatannol Inhibits TNF-Induced NF-KappaB Activation and NF-KappaB-Mediated Gene Expression Through Suppression of IkappaBalpha Kinase and p65 Phosphorylation", The Journal of Immunology, 169, (pp. 6490-6497), 2002.

Bain et al., "The Specificities of Protein Kinase Inhibitors: An Update", Biochem. Journal, 371, (pp. 199-204), 2003.

Brown, "The role of extracellular matrix proteins in the control of phagocytosis", Journal of Leukocyte Biology, vol. 39, (pp. 579-591), 1986.

Crouch, E., "Patholbiology of Pulmonary Fibrosis", Am J Physiol Lung Cell Mol Physiol 259, pp. L159-L184, 1990.

De Beer et al., "Isolation and Characterization of C-Reactive Protein and Serum Amyloid P Component in the Rat", Immunology 45, pp. 55-70, 1982.

De Paepe et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.

Duchemin et al., "Association of Non-Receptor Protein Tyrosine Kinases with the Fc Gamma RI/Gamma-Chain Complex in Monocytic Cells", The Journal of Immunology, 158, (pp. 865-871), 1997.

Du Clos, et al., "Reply to Human C-reactive protein does not bind to fc gamma RIIa on phagocytic cells", The Journal of Clinical Investigation, vol. 107, No. 5, pp. 643, 2001.

Emsley et al., "Structure of Pentameric Human Serum Amyloid P Component", Nature 367, pp. 338-345, 1994.

Ghazizadeh et al., "Physical and Fuctional Association of Src-Related Protein Tyrosine Kinases with Fc Gamma-RII in Monocytic THP-1 Cells", The Journal of Biological Chemistry, vol. 269, No. 12, (pp. 8878-8884), 1994.

Grazia, et al., "Suppression of IL-12 Transcription in Macrophages Following Fc Receptor Ligation", The Journal of Immunology, vol. 166, (pp. 4498-4506), 2001.

Gregory et al., "The DNA Sequence and Biological Annotation of Human Chromosome 1", Nature 441, pp. 315, 2006.

Hohenester et al., "Crystal Structure of a Decameric Complex of Human Serum Amyloid P Component with Bound dAMP", J. Mol. Biol. 269, pp. 570-578, 1997.

Huang et al., "The Monocyte Fcgamma receptors FcgammaRI/gamma and FcgammaRIIA Differ in their Interaction with Syk and with Src-Related Tyrosine Kinases", Journal of Leukocyte Biology, vol. 76, (pp. 491-499), 2004.

Junqueira et al., "Picrosirius Straining Plus Polarization Microscopy, A Specific Method for Collagen Detection in Tissue Sections", Histochem. J 11, pp. 447-455, 1979.

Kiernan et al., "Proteomic Characterization of Novel Serum Amyloid P Component Variants from Human Plasma and Urine", Proteomics 4, (pp. 1825-1829), 2004.

Kisseleva et al., Bone Marrow-Derived Fibrocytes Participate in Pathogenesis of Liver Fibrosis, 45 Journal of Hepatology, pp. 429-438, 2006.

Korade-Mirnics et al., "Src Kinase-Mediated Signaling in Leukocytes", Journal of Leukocyte Biology, vol. 68, (pp. 603-613), 2000.

Lai et al., "Potent Small Molecule Inhibitors of Spleen Tyrosine Kinase (Syk)", Bioorganic & Medicinal Chemistry Letters 13, (pp. 3111-3114), 2003.

Lei et al., "Genomic DNA Sequence for Human C-Reactive Protein", J. Biol. Chem. 260, pp. 13377-13383, 1985.

Liu et al., "Human Plasma N-Glycoproteome Analysis by Immunoaffinity Subtraction, Hydrazide Chemistry, and Mass Spectrometry", J. Proteome Res. 4, pp. 2070-2080, 2005.

Mantzouranis et al., "Human Serum Amyloid P Component", cDNA Isolation, Complete Sequence of Pre-Serum Amyloid P Component, and Localization of the Gene to Chromosome, The Journal of Biological Chemistry, vol. 260, No. 12, pp. 7752-7756, 1985.

Murphy et al., "Extrahepetic Transcription of Human C-Reactive Protein", Journal of Experimental Medicine, vol. 73, (pp. 495-498), 1991.

Ohnishi et al., "Isolation and Characterization of the Complete Complementary and Genomic DNA Sequences of Human Serum Amyloid P Component", J. Biochem. 100, pp. 849-858, 1986.

Oliveira et al., "Primary Structure of Human C-Reactive Protein", The Journal of Biological Chemistry, vol. 254, No. 2, (pp. 489-502), 1979.

Osmand et al., Partial Amino-Acid Sequences of Human and Rabbit C-Reactive Proteins: Homology with Immunoglobulins and Histocompatibility AntigensProc. Natl. Acad. Sci. U.S.A. vol. 74, No. 3, (pp. 1214-1218), 1977.

Pachence, et al., "Tissue-Activated Delivery—Novel Methods for Site-Directed Drug Delivery", Drug Delivery Technology, vol. 3, No. 1, (pp. 40-45.), 2003.

Pepys et al., "Human Serum Amyloid P Component is an Invariant Constituent of Amyloid Deposits and has a Uniquely Homogeneous Glycostructure", Proc. Natl. Acad. Sci. U.S.A., vol. 91, (pp. 5602-5606), 1994.

Pontet, et al., "One step preparation of both human C-reactive protein and CIt", FEBS Letters, vol. 88, No. 2, pp. 172-175, 1978.

Prelli et al., "The Primary Structure of Human Tissue Amyloid P Component From a Patient with Primary Idiopathic Amyloidosis", The Journal of Biological Chemistry, vol. 260, No. 24, (pp. 12895-12898), 1985.

Russo et al., "Liver Fibrosis; Bone Marrow Functionality Contributes to Liver Fibrosis", 130(6) Gastroenterology Week Jul. 31, 2006, (pp. 83-84), 2006.

Sada et al., "Structure and Function of Syk Protein-Tyrosine Kinase", The Japanese Biochemical Society, vol. 130, No. 2, (pp. 177-186), 2001.

Shrive et al., "Three Dimensional Structure of Human C-Reactive Protein", Nature Structural Biology, vol. 3, No. 4, (pp. 346-353), 1996.

Sjoeblom et al., "The Consensus Coding Sequences of Human Breast and Colorectal Cancers", Science vol. 314, www.sciencemag.org, (pp. 268-274), 2006.

Srinivasan et al., "Comparative Analyses of Pentraxins: Implications for Protomer Assembly and Ligand Binding", Structure, vol. 2, No. 11, (pp. 1017-1027), 1994.

Su et al., "Distinct Mechanisms of STAT Phosphorylation Via the Interferon-Alpha/Beta Receptor—Selective Inhibition of STAT3 and STAT5 by Piceatannol", The Journal of Biological Chemistry, vol. 275, No. 17 (pp. 12661-12666), 2000.

The MGC Project Team, "The Status, Quality, and Expansion of the NIH Full-Length cDNA Project: The Mammalian Gene Collection (MGC)", Genome Research, 14, pp. 2121-2127, 2004.

Thompson et al., "Human Plasma P Component: Isolation and Characterization", Biochemistry, vol. 17, No. 20, (pp. 4304-4311), 1978.

Thompson et al., "The Physiological Structure of Human C-Reactive Protein and its Complex with Phosphocholine", Structure, vol. 7, No. 2, (pp. 169-177), 1999.

Tridandapani et al., "Regulated Expression and Inhibitory Function of FcgammaRIIb in Human Monocytic Cells", The Journal of Biological Chemistry, vol. 277, No. 7, (pp. 5082-5089), 2002.

Tucci et al., "Biosynthesis and Postsynthetic Processing of Human C-Reactive Protein", The Journal of Immunology, vol. 131, No. 5, pp. 2416-2419, 1983.

Turner et al., "Tyrosine Kinase SYK: Essential Functions for Immunoreceptor Signalling", Review Immunology Today, vol. 21, No. 3 (pp. 148-154), 2000.

Underwood et al., SB 239063, "A p38 MAPK Inhibitor, reduces Neutrophilia, Infamatory Cytokines, MMP-9, and Fibrosis in Lung", Am J Physiol Lung Cell Mol Physiol, vol. 279, pp. L895-L902, 2000.

Vidal et al., "Inducible expression of PTX3, a new member of the pentraxin family, in human mononuclear phagocytes", Blood, vol. 84, No. 10, (pp. 3483-3493), 1994.

Wegiel et al., "Vascular Fibrosis and Calcification in the Hippocampus in Aging, Alzheimer Disease, and Down Syndrome", Acta Neuropathol, vol. 103 (pp. 333-343), 2001.

Whitehead et al., "Isolation of Human C-Reactive Protein Complementary DNA and Localization of the Gene to Chromosome 1", Science, vol. 221, No. 4605, pp. 69-71. http://www.jstor.org/stable/1691455, 1983.

Woo et al., "Characterization of Genomic and Complementary DNA Sequence of Human C-Reactive Protein, and Comparison with the Complementary DNA Sequence of Serum Amyloid P Component", The Journal of Biological Chemistry, vol. 260, No. 24, (pp. 13384-13388), 1985.

Zheng et al., "Piceatannol, a Stilbene Phytochemical, Inhibits Mitochondrial F0F1-ATPase Activity by Targeting the F1 Complex", Biochemical And Biophysical Research Communications, vol. 261, No. 2, (pp. 499-503), 1999.

International Search Report, PCT/US2003/041183, WO 2004/059318 (5 pages), 2004.

International Search Report, PCT/US2003/040957, WO 2004/058292 (7 pages), 2004.

Examination Report, European Patent Application No. 03 800 146.7 (5 pages), 2007.

International Search Report, PCT/US2006/005229, WO 2007/094776 (33 pages), 2007.

Examination Report, European Patent Application No. 08165673.8 (5 pages), 2008.

European Office Action; Application No. 03 814 319.4-2404; pp. 8, Apr. 21, 2009.

Australian Office Action; Application No. 2003299873; pp. 2, Apr. 23, 2009.

Japanese Office Action; Application No. 2004-564024 dated Jul. 7, 2010; pp. 3.

Schwalbe et al.; "Pentraxin Family of Proteins Interact Specifically with Phosphorylcholine and/or Phosporylethanolamine"; Biochemistry, vol. 31; pp. 4907-4615, 1992.

Weimann et al.; "Studies of Wound Healing: Effects of Calcium D-Panthothenate on the Migration, Proliferation and Protein Synthesis of Human Dernal Fibroblasts in Culture"; Internat. J. Vit. Nutr. Res., 69(2); pp. 113-119.

Gehring et al.; "Effect of Topically Applied Dexpanthenol on Epidermal Barrier Function and Stratum Corneum Hydration"; Arzneim.-Forsch./Drug Res.; 50(11); pp. 7.

Ishaque et al.; "Role of Vitamins in Determining Apoptosis and Extent of Suppression by bcl-2 During hybridoma Cell Culture"; Apoptosis; vol. 7, No. 3; pp. 231-239.

\* cited by examiner

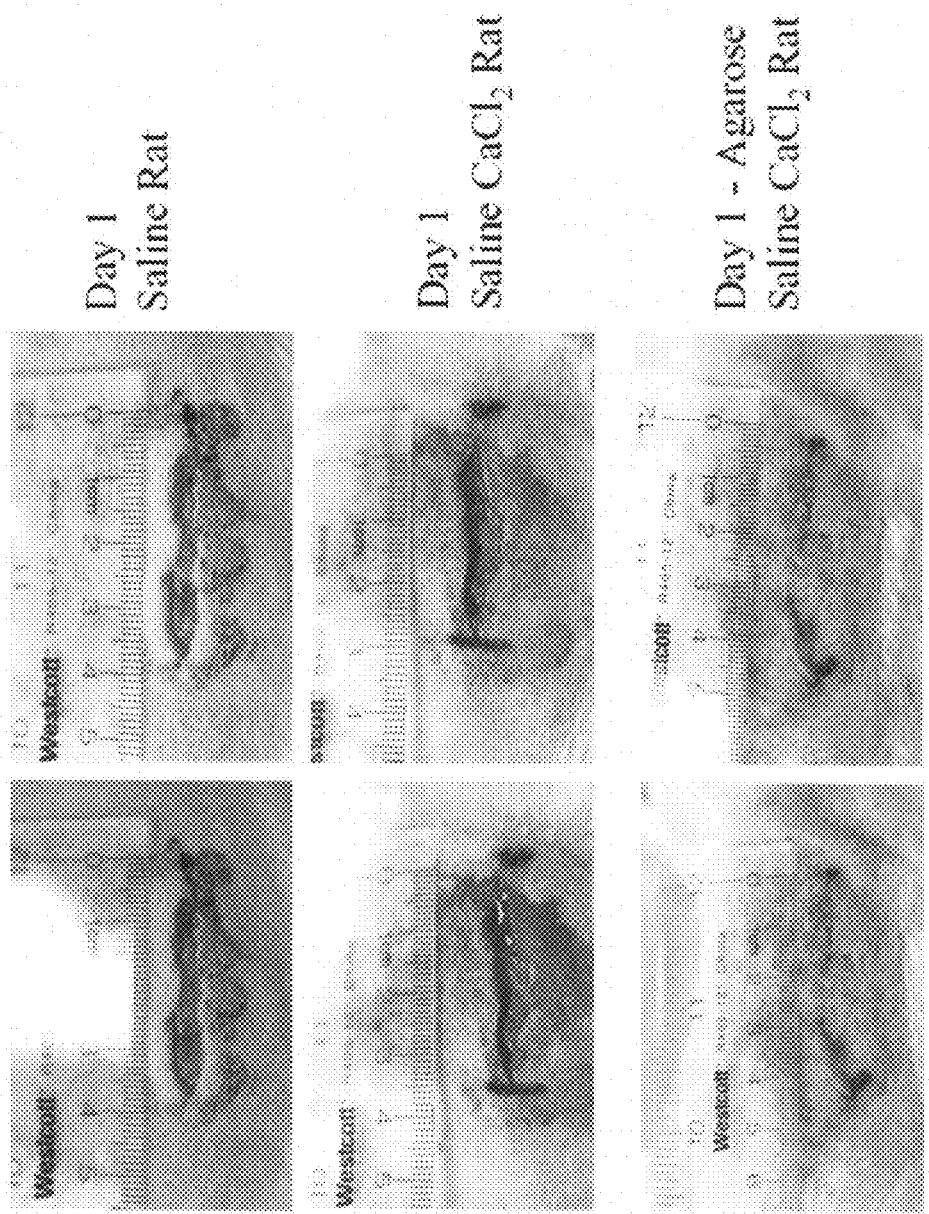

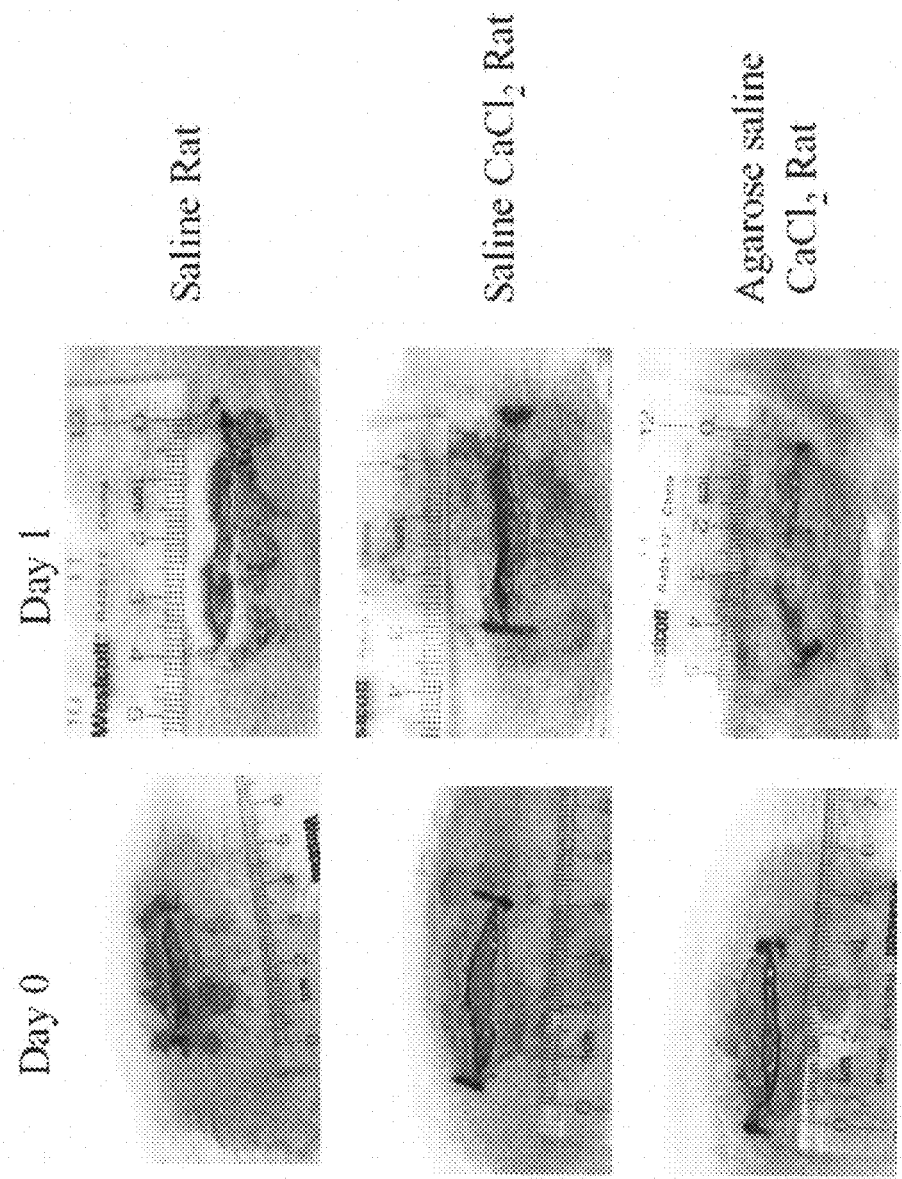

SEQUENCE LISTING

```
<160> NUMBER OF SEQ ID NOS: 8

<210> SEQ ID NO 1
<211> LENGTH: 25
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein regions
      that are not homolgous to CRP.

<400> SEQUENCE: 1

Lys Glu Arg Val Gly Glu Tyr Ser Leu Tyr Ile Gly Arg His Lys Val
1               5                   10                  15

Thr Ser Lys Val Ile Glu Lys Phe Pro
            20                  25

<210> SEQ ID NO 2
<211> LENGTH: 12
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein regions
      that are not homolgous to CRP.

<400> SEQUENCE: 2

Ile Leu Ser Ala Tyr Gln Gly Thr Pro Leu Pro Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein regions
      that are not homolgous to CRP.

<400> SEQUENCE: 3

Ile Arg Gly Tyr Val Ile Ile Lys Pro Leu Val
1               5                   10

<210> SEQ ID NO 4
<211> LENGTH: 6
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.
```

```
<400> SEQUENCE: 4

Val Phe Val Phe Pro Arg
1               5

<210> SEQ ID NO 5
<211> LENGTH: 10
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 5

Val Gly Glu Tyr Ser Leu Tyr Ile Gly Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 6

Ala Tyr Ser Leu Phe Ser Tyr Asn Thr Gln Gly Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 7

Gln Gly Tyr Phe Val Glu Ala Gln Pro Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: OTHER INFORMATION: Description of Artificial
      Sequence: derived from human Serum Amyloid P (SAP) protein.

<400> SEQUENCE: 8

Ile Val Leu Gly Gln Glu Gln Asp Ser Tyr Gly Gly Lys
1               5                   10
```

WOUND HEALING DRESSING FOR ENHANCING FIBROCYTE FORMATION

PRIORITY CLAIM

The present application is a continuation-in-part under 35 U.S.C. §120 of PCT patent application serial number PCT/US2003/041183, filed Dec. 22, 2003 and titled "Methods of Detecting the Inhibition of Fibrocyte Formation and Methods and Compositions for Enhancing Fibrocyte Formation", published in English as WO 04/059318 on Jul. 22, 2004; which claims priority to the following: U.S. Provisional Patent Applications: U.S. 60/436,046, filed Dec. 23, 2002; U.S. 60/436,027, filed Dec. 23, 2002; U.S. 60/515,776, filed Oct. 30, 2003; U.S. 60/519,467, filed Nov. 12, 2003; and U.S. 60/525,175 filed Nov. 26, 2003. Pertinent parts of all above applications are incorporated by reference herein.

TECHNICAL FIELD

The present invention relates to the ability of SAP to suppress the differentiation of monocytes into fibrocytes. Accordingly, it may include compositions and methods for increasing such differentiation. These compositions and methods may be useful in a variety of applications in which increased fibrocyte formation is beneficial, such as wound healing. The invention may additionally include methods for detecting problems in the ability of monocytes to differentiate into fibrocytes or for SAP to inhibit this differentiation. These problems may be correlated with a disease or may be drug-induced.

BACKGROUND

Fibrocytes

Inflammation is the coordinated response to tissue injury or infection. The initiating events are mediated by local release of chemotactic factors, platelet activation, and initiation of the coagulation and complement pathways. These events stimulate the local endothelium, promoting the extravasation of neutrophils and monocytes. The second phase of inflammation is characterized by the influx into the tissue of cells of the adaptive immune system, including lymphocytes. The subsequent resolution phase, when apoptosis of the excess leukocytes and engulfment by tissue macrophages takes place, is also characterized by repair of tissue damage by stromal cells, such as fibroblasts.

Both IL-4 and IL-13 are potent activators of the fibrotic response. IL-4 in known to enhance wound repair and healing. IL-13 has a high degree of homology with IL-4 and in many systems they act in a similar manner. However, key differences have been found in the function of these two proteins in various circumstances. For instance, IL-13 is more dominant in resisting infection by intestinal nematodes and intracellular parasites, such as *Leishmania*. IL-13 also plays a much more significant role than IL-4 in asthma. In contrast, IL-4 is more dominant than IL-13 in stimulating B cell production of immunoglobulin and in T cell survival and differentiation.

TGFβ, which is also known to play a role in wound healing, had been shown to facilitate fibrocyte differentiation into myofibroblasts, which are further associated with wound healing.

Although IL-4, IL-13, TGFβ and various other factors are known play a role in the fibrotic response, the source of fibroblasts responsible for repair of wound lesions or in other fibrotic responses is controversial. The conventional hypothesis suggests that local quiescent fibroblasts migrate into the affected area, produce extracellular matrix proteins, and promote wound contraction or fibrosis. An alternative hypothesis is that circulating fibroblast precursors (called fibrocytes) present within the blood migrate to the sites of injury or fibrosis, where they differentiate and mediate tissue repair and other fibrotic responses.

Fibrocytes are known to differentiate from a CD14+ peripheral blood monocyte precursor population. Fibrocytes express markers of both hematopoietic cells (CD45, MHC class II, CD34) and stromal cells (collagen types I and III and fibronectin). Mature fibrocytes rapidly enter sites of tissue injury where they secrete inflammatory cytokines. Once there, fibrocytes can function as antigen presenting cells (APCs), thereby inducing antigen-specific immunity. Fibrocytes are also capable of secreting extracellular matrix proteins, cytokines and pro-angiogenic molecules, which may aid in wound repair.

Fibrocytes are also associated with a variety of other processes and disorders. They are associated with the formation of fibrotic lesions after *Schistosoma japonicum* infection in mice and are also implicated in fibrosis associated with autoimmune diseases. Fibrocytes have also been implicated in pathogenic fibrosis such as that associated with radiation damage, Lyme disease and pulmonary fibrosis. CD34+ fibrocytes have also been associated with stromal remodeling in pancreatitis and stromal fibrosis, whereas lack of such fibrocytes is associated with pancreatic tumors and adenocarcinomas. This correlation may relate to the ability of fibrocytes to function as APCs. Finally, fibrocytes have been shown to promote angiogenesis by acting on endothelial cells.

Serum Amyloid P

Serum amyloid P (SAP), a member of the pentraxin family of proteins that include C-reactive protein (CRP), is secreted by the liver and circulates in the blood as stable pentamers. The exact biological role of SAP is still unclear, although it appears to play a role in both the initiation and resolution phases of the immune response. SAP binds to sugar residues on the surface of bacteria leading to their opsonisation and engulfment. SAP also binds to free DNA and chromatin generated by apoptotic cells at the resolution of an immune response, thus preventing a secondary inflammatory response. Molecules bound by SAP are removed from extracellular areas due to the ability of SAP to bind to all three classical Fcγ receptors (FcγR), with a preference for FcγRI (CD64) and FcγRII (CD32). After receptor binding, SAP and any attached molecule are likely engulfed by the cell.

FcγR are necessary for the binding of IgG to a wide variety of hematopoietic cells. Peripheral blood monocytes express both CD64 and CD32, whereas tissue macrophages express all three classical FcγR. A subpopulation of monocytes also express CD16 (FcγRII).

Clustering of FcγR on monocytes by IgG, either bound to pathogens or as part of an immune complex, initiates a wide variety of biochemical events. The initial events following receptor aggregation include the activation of a series of src kinase proteins. In monocytes, these include lyn, hck and fgr, which phosphorylate tyrosine residues on the ITAM motif of the FcR-γ chain associated with FcγRI and FcγRIII, or the ITAM motif with the cytoplasmic domain of FcγRII. Phosphorylated ITAMs lead to the binding of a second set of src kinases, including syk. Syk has been shown to be vital for phagocytosis of IgG-coated particles. However, the wide distribution of syk in non-hematopoietic cells and the evidence that syk is involved in both integrin and G-protein coupled receptor signaling, indicates that this molecule has many functions.

Both SAP and CRP augment phagocytosis and bind to Fcγ receptors on a variety of cells. CRP binds with a high affinity to FcγRII (CD32), a lower affinity to FcγRI (CD64), but does not bind FcγRIII (CD16). SAP binds to all three classical Fcγreceptors, with a preference for FcγRI and FcγRII, particularly FCγRI. Although there are conflicting observations on the binding of CRP to FcγR, both SAP and CRP have been shown to bind to Fc receptors and initiate intracellular signaling events consistent with FcγR ligation.

In human blood serum, males normally have approximately 32 μg/ml+/−7 μg/ml of SAP, with a range of 12-50 μg/ml being normal. Human females generally have approximately 24 μg/ml+/−8 μg/ml of SAP in blood serum, with a range of 8-55 μg/ml being normal. In human cerebral spinal fluid there is normally approximately 12.8 ng/ml SAP in human males and approximately 8.5 ng/ml in females. Combining male and female data, the normal SAP level in human serum is 26 μg/ml+/−8 μg/ml with a range of 12-55 μg/ml being normal. (The above serum levels are expressed as mean +/−standard deviation.)

SAP has been investigated primarily in relation to its role in amyloidosis. Recently, a drug, R-1-[6-[R-2-carboxy-pyrrolidin-1-yl]-6-oxo-hexanoyl] pyrrolidine-2-carboxylic acid (CPHPC) was developed to deplete SAP and thereby treat amyloidosis. However, this drug appears to have been applied systemically and not to have been used to treat wound healing or to have other localized or systemic effects.

Agar has been previously used as a wound dressing. However, it is not clear whether such previous wound dressings were capable of depleting SAP because they may not have contained appropriate chemical moieties or may have been used inappropriately. In any event, these previous wound dressing do not appear to have incorporated any additional wound healing factors. Further the dressings appear to have been used only for external wounds. Finally, it does not appear that these dressings incorporated purified SAP depleting chemicals or enhanced levels thereof.

SUMMARY

The present invention may include compositions and methods for binding SAP. Compositions operable to bind SAP may include CPHPC, the 4,6-pyruvate acetyl of beta-D-galactopyranose, phosphoethanolamines, and anti-SAP antibodies or fragments thereof. Such binding may occur in vivo.

The invention may also include compositions and methods for the depletion of SAP levels in a sample. The sample may be located in vitro or in vivo. In vivo the sample may include an entire organism or a portion thereof and depletion may be systemic or may be confined to a particular area, such as an organ or wound. The compositions may include those supplied directly or produced in the sample, for instance through expression of a transgene. Compositions operable to deplete SAP may include CPHPC, high EEO agarose, the 4,6-pyruvate acetyl of beta-D-galactopyranose, phosphoethanolamine, and anti-SAP antibodies or fragments thereof. SAP levels in a sample may also be depleted by interfering with its initial production or increasing degradation.

The invention may also include compositions and methods for the suppression of SAP activity. Suppression may be in a sample and may occur in vitro or in vivo. Compositions also include compositions supplied directly to a sample and those produced in the sample, such as by expression of a transgene. These compositions may act by decreasing SAP formation, decreasing the ability of SAP proteins to interact with monocytes, decreasing the ability of SAP proteins to interact with cofactors or decreasing the level of such cofactors, and interfering with SAP-induced signaling in monocytes, such as a pathway triggered by SAP binding to an FcγR. Compositions operable to suppress SAP activity may include anti-SAP antibodies and fragments thereof, particularly those targeted the Fc-binding region.

The invention may additionally include methods and compositions for promoting wound healing by depleting or, suppressing SAP in the region of a wound. Compositions may also include additional wound healing factors. In specific embodiments of the invention, wound healing compositions may include high EEO agarose, phosphoethanolamine agarose or $Ca^{2+}$ and combinations thereof. Cytokines such as IL-13, IL-4 and TGFβ may be added to these compositions.

Yet another aspect of the invention relates to compositions and methods for promoting fibrocyte formation by providing IL-4, IL-13 or a combination of the two to monocytes. The monocytes may be located in vitro or in vivo. IL-4 and IL-13 may be provided by an extraneous source, or endogenous production may be increased.

Finally, the invention may include assays to detect the ability of a sample to modulate fibrocyte differentiation from monocytes. In one embodiment, normal monocytes may be supplied with the sample. The sample may include normal SAP. It may also include SAP or a biological fluid from a patient such as a patient with a wound healing disorder, or it may include a potential drug. In another embodiment, the sample may include normal SAP while the monocytes may be derived from a patient and may be abnormal. In either type of assay, the effects on monocyte differentiation into fibrocytes may be compared with a normal control to detect any increases or decreases in monocyte differentiation as compared to normal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures form part of the present specification and are included to further demonstrate certain aspects of the present invention. The invention may be better understood by reference to one or more of these drawings in combination with the detailed description presented herein.

In FIG. 1A peripheral blood mononuclear cells (PBMC) at $2.5 \times 10^5$ per ml were cultured in serum-free medium for 3 or 6 days in the presence or absence of 0.1% human serum and then examined by microscopy for the appearance of fibroblast-like cells. Bar is 100 μm.

In FIG. 1B PBMC at $2.5 \times 10^5$ per ml were cultured in serum-free medium for 6 days in dilutions of human plasma. Cells were then air-dried, fixed, stained, and fibrocytes were enumerated by morphology. Results are expressed as mean±SD of the number of fibrocytes per $2.5 \times 10^5$ PBMCs (n=5 experiments). Stars indicate values that are statistically significant differences from the 0 SAP value.

In FIG. 3A fractions were analyzed by PAGE on a 4-20% reducing gel and stained with coomassie blue. M indicates molecular weight markers. Lane 1 contained plasma, lane 2 contained BaCl$_2$ supernatant, lane 3 contained wash 1, lane 4 contained wash 2, lane 5 contained BaCl$_2$ precipitate, lane 6 contained BaCl$_2$ precipitate, lane 7 contained heparin flow through, lane 8 contained the heparin fraction, lane 9 contained High Q flow through, lane contained the 10 High Q fraction, lane 11 contained the gel purified fraction. Lanes 1-5 diluted 1:500 in sodium phosphate buffer, lanes 6-11 undiluted.

Active fractions eluted off the High Q ion exchange column and gel slices were analyzed by 4-20% PAGE on a native gel in FIG. 3B and a reducing gel in FIG. 3C. NM indicates native gel markers, RM indicates reduced gel markers, in FIG. 3B lanes 1-3 are control gel samples, lane 4 contained active fraction. In FIG. 3D fractions were assessed by western blotting, using a rabbit anti-SAP antibody. Lanes 1-11 correspond to those in FIG. 3A.

FIG. 5A shows the effect on fibrocyte differentiation of depleting SAP from plasma with BioGel agarose beads. Number of fibrocytes found in an assay supplied with either plasma (open square) or BioGel depleted plasma (filled square) at a variety of dilutions is shown.

FIG. 5B shows the number of fibrocytes formed in an assay performed with no plasma or equal dilutions of plasma, Bio-Gel SAP depleted plasma, or anti-SAP antibody depleted plasma. Stars indicate statistically significant differences.

FIGS. 7A-7B show healing of the skin incisions shown in FIG. 6. FIG. 7A shows healing of skin incisions on three different rats after one day of treatment with either saline, saline with CaCl$_2$, or agarose with saline and CaCl$_2$. FIG. 7B shows a comparison of initial skin incisions on three different rats and healing after one day of treatment with either saline, saline with CaCl$_2$, or agarose with saline and CaCl$_2$.

FIG. 8A shows healing of skin incisions on three different rats after two days of treatment with either saline, saline with CaCl$_2$, or agarose with saline and CaCl$_2$. FIG. 8B shows a comparison of initial skin incisions on three different rats and healing after one and two days of treatment with either saline, saline with CaCl$_2$, or agarose with saline and CaCl$_2$.

DETAILED DESCRIPTION

Figure 1A:
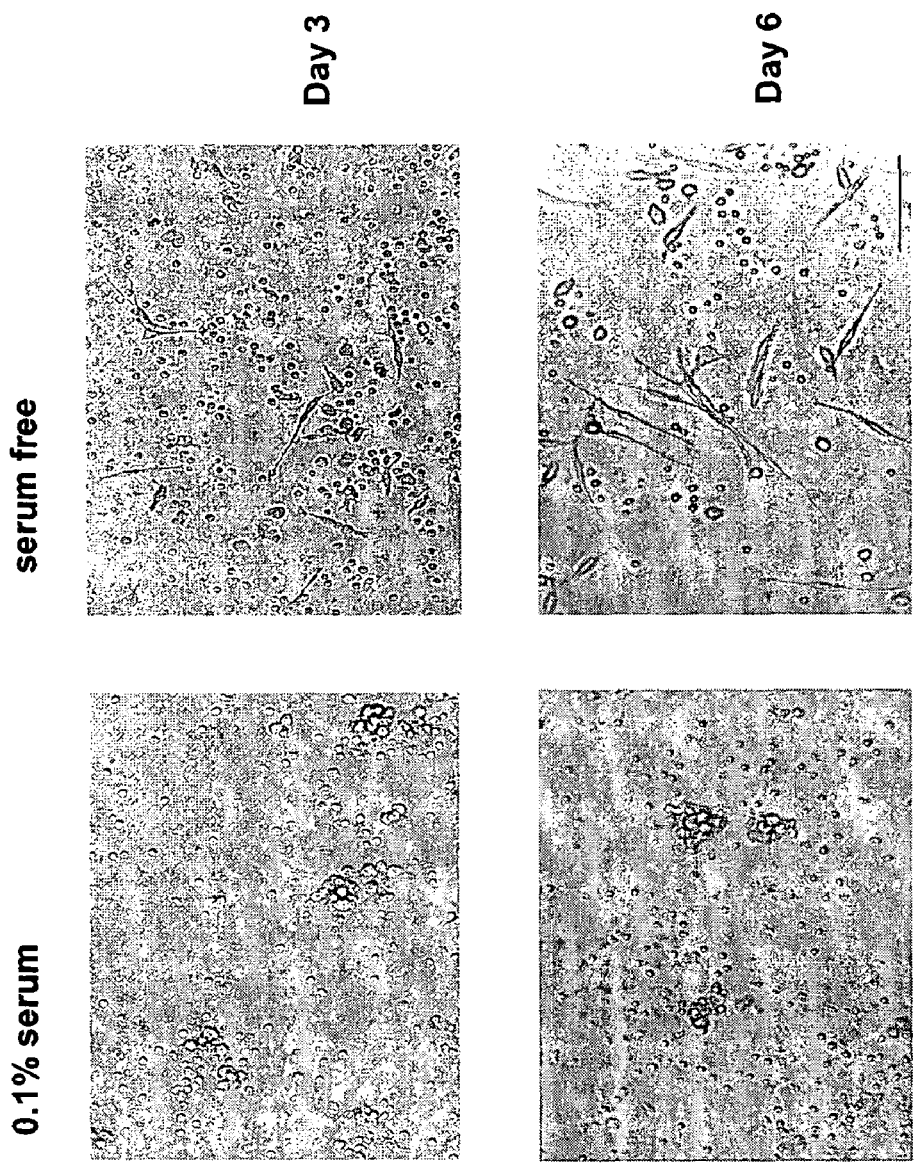
FIGS. 1A-1B illustrate the effects of serum and plasma on the rapid differentiation of fibroblast-like cells.

Fibrocytes are a distinct population of fibroblast-like cells derived from peripheral blood monocytes. Culturing CD14+ peripheral blood monocytes in the absence of serum or plasma leads to the rapid differentiation of fibrocytes. This process normally occurs within 48-72 hours and is suppressed by the presence of blood serum or plasma. Experiments described further herein have determined that this suppression is caused by SAP. Additional experiments have determined that, when monocytes are cultured in serum-free medium, differentiation into fibrocytes is enhanced by the presence of IL-4 or IL-13.

Binding of SAP

The present invention may include compositions and methods for binding SAP. Compositions may include CPHPC, the 4,6-pyruvate acetyl of beta-D-galactopyranose, ethanolamines, anti-SAP antibodies or fragments thereof, and DNA. Agarose may also be used to bind SAP. For example, High EEO agarose (Fisher Scientific Internation Inc., NH), Low EEO agarose (Fisher Scientific Internation Inc., NH), SeaKem® ME agarose (Cambrex Bioscience, NJ), SeaKem® SP agarose (Cambrex Bioscience, NJ), Bio-Gel A (BioRad Laboratories, CA), SP-Sepharose (Amersham Biosciences, UK) CL-Sepharose (Amersham Biosciences, UK), Heparin-agarose, Aspartic acid-agarose and Poly-lysine-agarose and derivatized agarose may all be used in embodiments of the invention.

These compositions may include purified chemicals, or the chemicals may be attached to another compound, for example a much larger compound, such as agarose or a biocompatible polymer (e.g. PEG, poly(amino acids) such as poly(glutamic acid), chitosan, other polysaccharides, and other biological polymers, or chemically modified versions thereof). Binding may occur in vitro or in vivo.

In a specific embodiment, SAP may be bound by a composition including approximately 1% w/v high EEO agarose. The composition may also include a cation, such as Mg$^{2+}$ or Ca$^{2+}$. For example, the agarose may include approximately 5 mM CaCl$_2$.

In other embodiments, the composition may include an antibody or antibody fragment that targets the portion of SAP functional in inhibiting fibrocyte formation from monocytes. In an exemplary embodiment, the functional portion of SAP may be selected from the region that does not share sequence homology with CRP, which has no effect on fibrocyte formation. For instance amino acids 65-89 KERVGEYSLYIGRH-KVTSKVIEKFP (SEQ ID NO:1) of SAP are not homologous to CRP. Amino acids 170-181 ILSAYQGTPLPA (SEQ ID NO:2) and 192-205 IRGYVIIKPLV (SEQ ID NO:3) are also not homologous. Additionally a number of single amino acid differences between the two proteins are known and may result in functional differences.

Depletion of SAP

Other aspects of the invention relate to compositions and methods for the depletion of SAP levels in a sample. The sample may be located in vitro or in vivo. In vitro samples may include tissue cultures, bioreactors, tissue engineering scaffolds and biopsies. In vivo the sample may include an entire organism or a portion thereof such as an organ or injury site. Depletion in vivo may be systemic or it may be confined to a particular area, such as an organ or wound.

Compositions for depletion of SAP may include those supplied directly to the sample. For instance all of the binding agents mentioned above may be supplied directly to the sample. They may be supplied in any form or formulation although those that do not substantially interfere with desired outcomes for the sample may be preferred.

Compositions for the depletion of SAP may also be produced in the sample, or in an organism containing the sample. For example, a transgene encoding an anti-SAP antibody may be introduced into the sample.

SAP may be directly depleted by a material that binds or sequesters SAP, such as agarose, CPHPC, 4,6-pyruvate acetyl of beta-D-galactopyranose, phosphoethanolamine agarose, anti-SAP antibodies, DNA analogs and carbohydrate analogs.

Depletion may also occur by degradation or inactivation of SAP such as through the use of SAP-specific proteases.

Other compositions may increase the rate of uptake of SAP and this decrease its availability.

Finally, SAP levels may also be depleted by interfering with its initial production or increasing its degradation. In a specific embodiment, SAP levels may be depleted in vivo by administering a composition that inhibits SAP production. Because SAP is primarily produced in the liver, in vivo suppression of SAP production should be easily attained, but will be systemic. Compositions that interfere with SAP production may act upon a signaling pathway that modulates SAP production.

Suppression of SAP Activity

The invention may also include compositions and methods for the suppression of SAP activity. Suppression may be in a sample and may occur in vitro or in vivo. Compositions may also include compositions supplied directly to a sample and those produced in the sample. Many such compositions may be SAP-binding compositions described above. In particular, compositions for the suppression of SAP activity may include antibodies selected as described above to bind to specific regions of SAP not homologous to CRP. Antibodies may also target the region of SAP that binds to FcγR or may compete with SAP for binding to the these receptors. Small peptides may also be able to block SAP binding to the FcγR or compete with SAP for binding to these receptors.

Compositions that suppress SAP activity may act by a variety of mechanisms including but not limited to: decreasing the ability of SAP proteins to interact with monocytes, decreasing the ability of SAP proteins to interact with cofactors or decreasing the level of such cofactors, and interfering with SAP-induced signaling in monocytes, such as a pathway triggered by SAP binding to an FcγR. This pathway is described in detail in Daeron, Marc, "Fc Receptor Biology", Annu. Rev. Immunology 15:203-34 (1997). In an exemplary embodiment a portion of the pathway that is not shared with other signaling cascades or only a limited number of non-critical signaling cascades may be selected for interference to minimize side-effects. For example, a composition may interfere with the Fc pathway by blocking syk kinase.

Effects of IL-4 and IL-13

Yet another aspect of the invention relates to compositions and methods for promoting fibrocyte formation by providing IL-4, IL-13 or a combination of the two to monocytes. The monocytes may be located in vitro or in vivo. IL-4 and IL-13 may be provided by an extraneous source, or endogenous production may be increased. More specifically, IL-4 or IL-13 may be provided at concentrations of between approximately 0.1 and 10 ng/ml.

Uses for Modulating Fibrocyte Formation

Depletion or suppression of SAP or supply of IL-4 or IL-13 in a sample may be used to increase fibrocyte differentiation from monocytes. This effect has many uses both in vitro and in vivo. For example, in vitro increased fibrocyte formation may be useful in tissue engineering. Production of fibrocytes in areas requiring vascularization may induce angiogenesis. In vitro, increased differentiation of monocytes to form fibrocytes may also be used for internal tissue engineering or for inducing angiogenesis in areas in need of new vasculature.

Additionally, increasing differentiation of monocytes into fibrocytes in vivo may promote wound healing or may be used for cosmetic surgery applications. Wound healing may benefit, inter alia, from the ability of fibrocytes to further differentiate into other cells such as myofibroblasts and from angiogenic effects of fibrocytes as well as the from their ability to function as APCs, thereby assisting in prevention or control of infection.

Because of the ability of fibrocytes to function as APCs, areas of chronic infection or areas that are infected but not readily reached by the immune system, such as cartilage, may also benefit from increased monocyte differentiation into fibrocytes.

Because pancreatic tumors and adenocarcinomas show lower levels of fibrocytes, increasing differentiation of monocytes into fibrocytes in these tissues may help slow the tumor progression or aid in remission.

Specific Formulations

Some compositions of the present invention may be provided in a variety of formulations.

In a specific example, the invention may include methods and compositions for promoting wound healing by depleting or suppressing SAP in the region of a wound. These wound healing compositions may include CPHPC, anti-SAP antibodies, 4,6-pyruvate acetyl of B-D-galactopyranose, such as found on high EEO agarose, ethanolamines, such as those found on phosphoethanolamine agarose, $Ca^{2+}$, and combinations thereof. Cytokines such as IL-13, IL-4, FGF and TGFβ may be added to these compositions.

In many patients only localized SAP depletion or inhibition or interference with a SAP-modulated pathway may be desirable. Many compositions within the scope of the present invention may be administered locally to such patients. For instance, administration of a composition may be topical, such as in an ointment, cream, solid, spray, vapor or wound dressing. Such topical formulations may include alcohol, water, disinfectants, other volatile substances, or any other pharmaceutically active agents, such as antibiotics and anti-infective agents, or pharmaceutically acceptable carriers. Local administration may also be by localized injection of a composition alone or in combination with another pharmaceutically active agent or pharmaceutically acceptable carrier.

Patients for whom localized administration of compositions that increase monocyte differentiation into fibrocytes may be advisable include but are not limited to: mild to moderate burn patients; patients who have suffered lacerations, including those inflicted during surgical procedures; patients suffering from diabetic complications, such as ulcers; patients with pressure ulcers or areas of low circulation internally; patients with abrasions, minor contusions or puncture wounds; patients with bullet or shrapnel wounds; patients with open fractures; patients in need of tissue growth for tissue engineering or cosmetic reasons; and immunosuppressed, hemophiliac or other patients who are likely to benefit from the more rapid healing of most wounds.

For patients with severe or numerous wounds or other disorders, more general administration of a composition to promote fibrocyte formation through an IV or other systemic injection may be appropriate. Patients for whom systemic administration of a SAP depleting or inhibiting agent may be helpful include, but are not limited to: severe burn patients; later stage peripheral arterial occlusive disease patients; and patients with general wound healing disorders.

Some formulations may be appropriate for local or systemic administration. Additionally, the therapeutic agent may be supplied in a solid form, such as a powder, then reconstituted to produce the formulation ultimately administered to a patient.

In an exemplary embodiment for the treatment of wound healing, high EEO agarose or phosphoethanolamine agarose may be administered as a would dressing. In this embodiment, the agarose may be at a concentration of approximately 1% (w/v) and may also contain approximately 5 mM $CaCl_2$. The wound dressing may be applied for any period of time. Although it may be applied continuously until the wound has closed (approximately two days or more), it may also only be applied for a short initial period, such as 12 hours. This initial removal of SAP from the wound may be sufficient to induce increased differentiation of monocytes into fibrocytes and improve wound healing.

In another exemplary embodiment, CPHPC may be administered systemically to promote healing of widespread or recalcitrant wounds. CPHPC has been previously administered in a range of 1.5 to 15 mg/kg/day by osmotic pumps in mice in amyloidosis experiments. CPHPC has also been administered in 1 mg/ml water concentrations in drinking water for mice. A 20 g mouse drinks approximately 3 ml of water per day, resulting in an intake of approximately 0.15 CPHPC mg/kg/day. Such ranges are therefore likely safe in humans to reduce SAP levels, although different ranges may provide optimal benefit for wound healing.

In other embodiments, the compositions may be provided in or on prosthetic devices, particularly surgically implanted prosthetic devices.

In some embodiments, the compositions may be provided in a slow-release gel or dressing, such as a plastic substrate. Compositions may also be provided as hydrogels.

Monocyte Differentiation Assays

Another aspect of the invention relates to assays to detect the ability of a sample to modulate fibrocyte differentiation from monocytes. In serum-free medium, normal monocytes form fibrocytes in two to three days. Normal serum, blood or other biological fluids suppress the formation of fibrocytes from normal monocytes over a specific dilution range. Thus the assay may be used to test whether a sample can modulate differentiation of monocytes into fibrocytes in serum-free medium. It may also be used to determine whether sample monocytes differentiate normally into fibrocytes in serum-free medium and if they respond normally to serum, SAP or other factors affecting this differentiation.

In a specific embodiment, the assay may be used to determine whether a patient's biological fluid has a decreased or increased ability to suppress monocyte differentiation into fibrocytes. If suppression by SAP is to be tested, any biological fluid in which SAP is normally or transiently present may be used, including whole blood, serum, plasma, synovial fluid, cerebral spinal fluid and bronchial fluid. An increased ability to suppress monocyte differentiation may be indicative of a wound healing disorder or other disorders, or the propensity to develop such a disorder. Although in many patients an increased ability of a biological fluid to suppress fibrocyte formation may be due to low levels of SAP, this is not necessarily the case. SAP may be present at normal levels, but exhibit decreased suppressive activity due to defects in the SAP itself or the absence or presence of a cofactor or other molecule. Methods of determining the more precise nature of the suppression problem, such as use of ELISAs, electrophoresis, and fractionation will be apparent to one skilled in the art.

The methodology described above may also be used to determine whether certain potential drugs that affect fibrocyte differentiation may or may not be appropriate for a patient.

In another specific embodiment, the assay may be used to determine if a patient's monocytes are able to differentiate into fibrocytes in serum-free medium and if they respond normally to a biological fluid, SAP or another composition. More particularly, if a patient with wound healing problems appears to have normal levels of SAP, it may be advisable to obtain a sample of the patient's monocytes to determine if they are able to differentiate in the absence of serum or SAP.

Finally, in another specific example, the assay may be used to test the effects of a drug or other composition on monocyte differentiation into fibrocytes. The assay may be used in this manner to identify potential drugs designed to modulate fibrocyte formation, or it may be used to screen for any potential adverse effects of drugs intended for other uses.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Inhibition of Fibrocyte Formation

While examining the possible role of cell density in the survival of peripheral blood T cells, it was observed that in serum-free medium PBMC gave rise to a population of fibroblast-like cells. These cells were adherent and had a spindle-shaped morphology (FIG. 1A). Approximately 0.5-1% of PBMC differentiated into fibroblast-like cells in serum-free medium, and this occurred in tissue culture treated plasticware and borosilicate and standard glass slides.

Figure 1B:
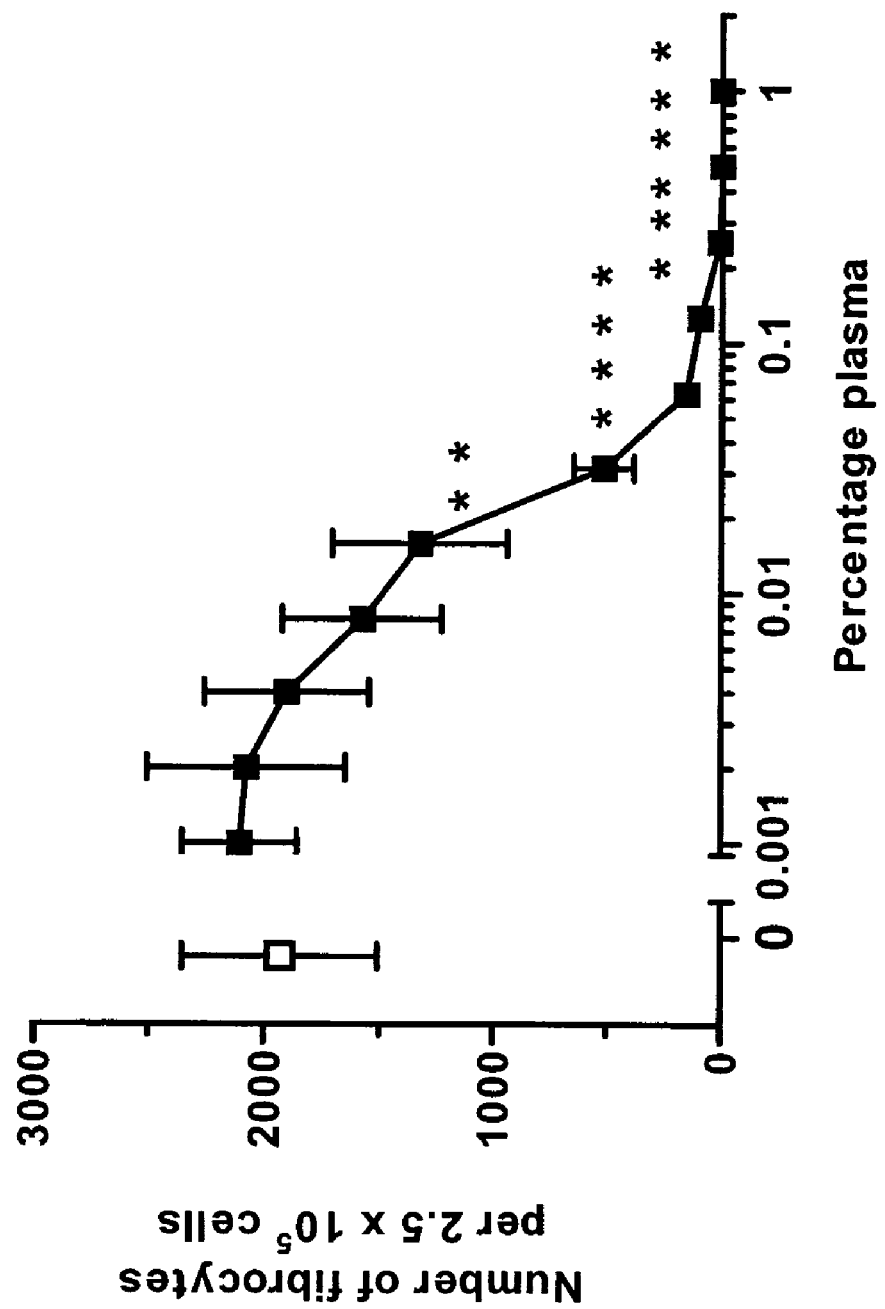

The rapid appearance of these cells, within 3 days of culture, was inhibited by human serum or plasma. To examine this process in more detail, PBMC were cultured at $5 \times 10^5$ cells per ml in serum-free medium containing increasing concentrations of human plasma for 6 days. When plasma was present at concentrations between 10% and 0.5%, the fibroblast-like cells did not differentiate (FIG. 1B). However, at or below 0.1% serum, fibroblast-like cells rapidly developed. The activity in the serum that inhibited fibrocyte formation was retained by a 30 kDa cutoff spin-filter (data not shown). If serum was heated to 56° C. for 30 minutes, the efficacy was reduced 10 fold, and heating to 95° C. abolished the inhibitory activity (data not shown).

These data suggested that that the inhibitory factor is a protein. As the inhibitory factor was present in human serum, it indicated that the activity was unlikely to be involved with the coagulation system. The inhibitory factor also appeared to be an evolutionary conserved protein as bovine, equine, caprine, and rat sera were also able to inhibit the appearance of these fibroblast-like cells (data not shown).

Example 2

Characterization of Fibroblast-Like Cells

The differentiation of these fibroblast-like cells from peripheral blood suggested that they might be peripheral blood fibrocytes. Fibrocytes are a population derived from peripheral blood monocytes that differentiate in vitro and in vivo into fibroblast-like cells. They rapidly enter wound sites and are capable of presenting antigens to T cells. Their phenotype is composed of both haematopoietic markers, such as CD45 and MHC class II, and stromal markers, such as collagen I and fibronectin. However in order to identify these cells, PBMC were generally cultured for 1-2 weeks in medium containing serum.

To characterize whether the cells observed in the system were fibrocytes, PBMC were depleted of T cells with anti-CD3, B cells with anti-CD19, monocytes with anti-CD14 or all antigen presenting cells with anti-HLA class II and then cultured in serum-free conditions for 6 days. Depletion of PBMC with anti-CD3 or anti-CD19 did not deplete fibroblast-like cells from PBMC when cultured in serum-free cultures (data not shown). Depletion of antigen presenting cells with anti-HLA class II or monocytes with anti-CD14 antibody did prevent the appearance of fibroblast-like cells, indicating that the fibroblast-like cells are derived from monocytes and not a dendritic cell population.

Figure 2:
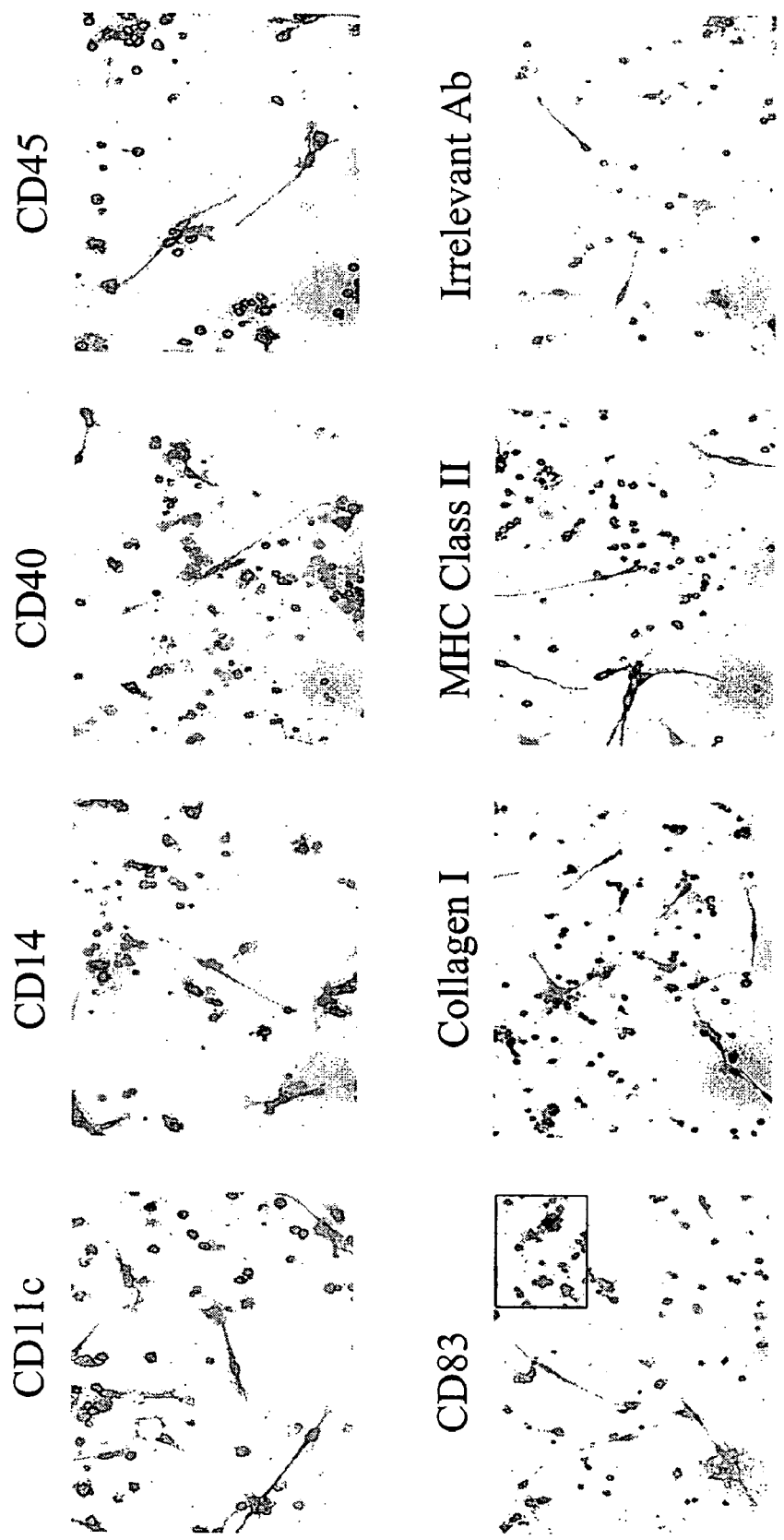
FIG. 2 illustrates the expression of surface molecules on fibroblast-like cells. PBMC were cultured on glass slides in serum-free medium for 6 days. Cells were air-dried and analyzed by immunohistochemistry. Monoclonal antibodies used were as indicated, and identified by biotin-conjugated goat anti-mouse Ig followed by ExtrAvidin peroxidase. Cells were counterstained with Mayer's haematoxylin to identify nuclei. Positive staining was identified by brown staining, nuclei were counterstained blue. An insert for CD83 was used to indicate positive staining on a dendritic cell.

To further characterize the fibroblast-like cells, PBMC were cultured in serum-free medium for 5 days on glass slides. Cells were then air-dried, fixed in acetone and labeled with a variety of antibodies (Table 1 and FIG. 2). Fibrocytes express CD11a, CD11b, CD45, CD80, CD86, MHC class II, collagen I, fibronectin, the chemokine receptors CCR3, CCR5, CCR7, CXCR4 and α-smooth muscle actin. In the above culture conditions, the fibroblast-like cells in the present experiment also expressed all these markers. Fibrocytes are negative for CD1a, CD3, CD19, CD38 and vWF, as were the fibroblast-like cells in the present experiment. Based on these data it appears that the fibroblast-like cells observed in the experiments were fibrocytes. Further experiments were conducted to extend this phenotype. In the above conditions, the fibrocytes expressed several β1 integrins including α1 (CD49a), α2 (CD49b), α5 (CD49e), β1 (CD29) and β3 (CD61) along with high levels of β2 (CD18), but were negative for α3, α4, α6 α4β7, αE and CLA (FIG. 2 and Table 1).

TABLE 1

Expression of surface markers on Fibrocytes

| Marker | Alternative Name | Fibrocyte Expression |
| --- | --- | --- |
| CD11a | LFA-1 | positive |
| CD11b | Mac-1 | positive |
| CD11c | | positive |
| GD13 | | positive |
| GD18 | β2 integrin | positive |
| CD29 | β1 integrin | positive |
| CD34 | | positive |
| CD40 | | weak positive |
| CD45 | LCA | positive |
| CD49a | α1 integrin | weak positive |
| CD49b | α2 integrin | negative |
| CD49e | α5 integrin | positive |
| CD51 | | positive |
| CD54 | ICAM-1 | positive |
| CD58 | LFA-3 | positive |
| CD61 | β3 integrin | positive |
| CD80 | B7-1 | weak positive |
| CD86 | B7-2 | positive |
| GD105 | Endoglin | positive |
| CD148 | | positive |
| MHC Class II | | positive |
| CD162 | PSGL-1 | positive |
| CCR1 | | weak positive |
| CCR3 | | weak positive |
| CCR4 | | weak positive |
| CCR5 | | weak positive |
| CCR7 | | weak positive |
| CCR9 | | weak positive |
| CXCR1 | | positive |
| CXCR3 | | positive |
| CXCR4 | | weak positive |
| Collagen I | | positive |
| Collagen III | | positive |
| Fibronectin | | positive |
| α Smooth Muscle Actin | | positive |
| Vimentin | | positive |
| CD1a | | negative |
| CD3 | | negative |
| CD10 | | negative |
| CD14 | | negative |
| GD19 | | negative |
| CD25 | | negative |
| CD27 | | negative |
| CD28 | | negative |
| CD38 | | negative |
| CD49C | α3 integrin | negative |
| CD49d | α4 integrin | negative |
| CD49f | α6 integrin | negative |
| CD69 | | negative |
| CD70 | CD27-L | negative |
| CD90 | | negative |
| CD103 | αE integrin | negative |
| GD109 | | negative |
| CD154 | CD40-L | negative |
| α4β7 | | negative |
| CLA | | negative |
| CCR2 | | negative |
| CCR6 | | negative |
| CXCR2 | | negative |
| CXCR5 | | negative |
| CXCR6 | | negative |
| Cytokeratin | | negative |
| vWF | | negative |

To obtain the data in Table 1, PBMC were cultured in the wells of 8 well glass slides at $2.5 \times 10^5$ cells per ml (400 μl per well) in serum-free medium for 6 days. Cells were then air dried, fixed in acetone and stained by immunoperoxidase. Cells were scored positive or negative for the indicated antigens, compared to isotype-matched control antibodies.

Example 3

Characterization of the Fibrocyte Inhibitory Factor

The initial characterization of the serum factor that prevents rapid fibrocyte differentiation indicated that the factor was a heparin-binding molecule that eluted off an ion exchange column (High Q) as one of four proteins. By sequencing tryptic fragments of protein in a band cut from a native gel, one of these proteins was identified as C4b-binding protein (C4BP). C4b-binding protein is a 570 kDa protein, composed of seven alpha chains (70 kDa) and usually a single beta chain (40 kDa), which is involved in regulating the decay of C4b and C2a components of the complement system. C4BP also interacts with the vitamin K-dependent anticoagulant protein S. The C4BP/Protein S complex can be purified from serum or plasma using BaCl2 precipitation.

Figure 3:
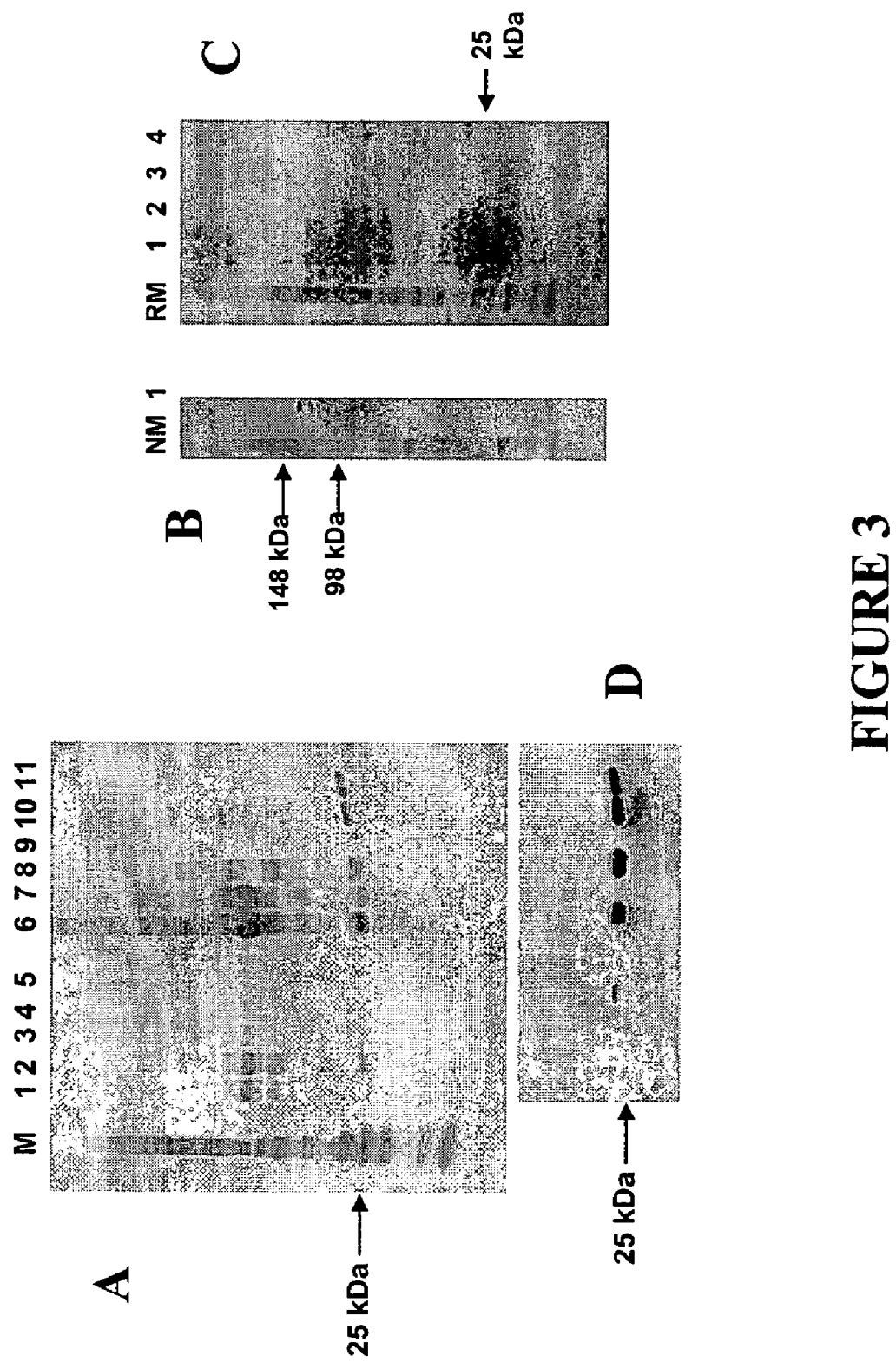
FIG. 3 illustrates the characterization of the molecule present in plasma that inhibits fibrocyte differentiation. Citrated plasma was treated with BaCl$_2$ and the precipitated material was collected by centrifugation and dialyzed against 10 mM sodium phosphate containing 10 mM EDTA and protease inhibitors. This material was then fractionated by heparin and ion exchange chromatography.

To assess whether C4BP, or an associated protein, was the factor responsible for inhibiting fibrocyte differentiation, citrated plasma was treated with BaCl2. The inhibitory factor was present in the BaCl2 precipitate (FIG. 3 and Table 2). This fraction was applied to a heparin column and the fractions, eluted by increasing concentrations of NaCl, were assessed for their ability to inhibit monocyte to fibrocyte differentiation in serum free medium. The active factor was eluted off the heparin column in a peak at 200 mM NaCl (FIG. 3 and Table 2). A slight increase in the yield suggested that this step may have removed a factor that slightly interfered with the activity of the factor.

The fractions from the 200 mM peak were pooled and further fractionated by High Q ion exchange chromatography. A small peak eluting at 300 mM NaCl contained activity that inhibited fibrocyte differentiation. Analysis of the proteins present in this fraction indicated that the major band was a 27 kDa protein. Although the ion exchange chromatography led to a reduction in the amount of SAP recovered (FIG. 3A, lanes 8-10 and FIG. 3D, lanes 8-10) this step did remove several contaminating proteins. After the ion exchange step the only discernable contaminant was albumin at 65 kDa (FIG. 3A, lane 10).

The high Q fraction was concentrated and fractionated by electrophoresis on a non-denaturing polyacrylamide gel, followed by elution of the material in gel slices. A single band that migrated at approximately 140 kDa was able to inhibit differentiation (FIG. 3B). This band had a molecular weight of 27 kDa on a reducing polyacrylamide gel, suggesting that the native conformation of the protein was a pentamer (FIG. 3C). This band was excised from the gel, digested with trypsin and analyzed by MALDI mass spectrometry. Three major and two minor peptides were identified: VFVFPR (SEQ ID NO: 4), VGEYSLYIGR (SEQ ID NO: 5), AYSLFSYNTQGR (SEQ ID NO: 6), QGYFVEAQPK (SEQ ID NO: 7) and IVLGQEQDSYGGK (SEQ ID NO: 8). These sequences exactly matched amino acid sequences 8-13, 68-77, 46-57, 121-130 and 131-143 of serum amyloid P.

To confirm that the active fractions contained SAP, fractions collected from column chromatography were analyzed by western blotting (FIG. 3D). The presence of SAP at 27 kDa was detected in all fractions that inhibited fibrocyte differentiation (FIG. 3D, lanes 6, 8, 10 and 11). A considerable amount of SAP was present in the supernatant from the BaCl2 precipitation step indicating that this procedure was inefficient, with the recovery of only approximately 10-15% of the fibrocyte inhibitory activity in the BaCl2 pellet (FIG. 3A lane 2). In order to remove the known problem of anti-SAP antibodies binding to immunoglobulins when used with western blotting, the antibody was pre-incubated with human IgG bound to agarose. Fractions were also analyzed for the presence of CRP, C4BP and protein S. Western blotting indicated that C4BP and Protein S were present in plasma, and in the barium precipitation, but were absent from the active fractions collected from heparin chromatography (data not shown).

TABLE 2

Recovery of protein and fibrocyte inhibitory activity from fractionated human plasma

| | Volume (ml) | Protein (mg/ml) | Total protein (mg) | Yield (%) |
|---|---|---|---|---|
| Plasma | 250 | 70 | 17,500 | 100 |
| BaCl$_2$ supernatant | 240 | 60 | 14,400 | 82.3 |
| BaCl$_2$ precipitate | 31 | 1 | 31 | 0.18 |
| Heparin fraction | 4.3 | 0.25 | 1.075 | 0.006 |
| High Q fraction | 1.96 | 0.05 | 0.098 | 0.00056 |
| Gel slice | 0.075 | 0.025 | 0.0018 | 0.00001 |

| | Activity (U/ml) | Total activity (U) | Yield (%) | Specific activity (U/mg) |
|---|---|---|---|---|
| Plasma | 10,000 | $2.5 \times 10^6$ | 100 | 143 |
| BaCl$_2$ supernatant | 6,666 | $1.6 \times 10^6$ | 64 | 111 |
| BaCl$_2$ precipitate | 1,666 | $5.1 \times 10^4$ | 2 | 1,645 |
| Heparin fraction | 500 | 2,150 | 0.086 | 2000 |
| High Q fraction | 400 | 720 | 0.029 | 7,300 |
| Gel slice | 2000 | 150 | 0.006 | 80,000 |

Plasma was fractionated by BaCl$_2$ precipitation, heparin and ion exchange chromatography. Protein concentrations were assessed by spectrophotometry at 280 nm. Inhibition of fibrocyte differentiation was assessed by morphology. The fibrocyte inhibitory activity of a sample was defined as the reciprocal of the dilution at which it inhibited fibrocyte differentiation by 50%, when added to serum-free medium.

SAP may also be detected by ELISA using the following methodology:

Maxisorb 96 well plates (Nalge Nunc International, Rochester, N.Y.) were coated overnight at 4° C. with monoclonal anti-SAP antibody (SAP-5, Sigma) in 50 mM sodium carbonate buffer pH 9.5. Plates were then incubated in Tris buffered saline pH 7.4 (TBS) containing 4% BSA (TBS-4% BSA) to inhibit non-specific binding. Serum and purified proteins were diluted to 1/1000 in TBS-4% BSA, to prevent SAP from aggregating and incubated for 60 minutes at 37° C. Plates were then washed in TBS containing 0.05% Tween-20. Polyclonal rabbit anti-SAP antibody (BioGenesis) diluted 1/5000 in TBS-4% BSA was used as the detecting antibody. After washing, 100 pg/ml biotinylated goat F(ab)$_2$ anti-rabbit (Southern Biotechnology Inc.) diluted in TBS-4% BSA was added for 60 minutes. Biotinylated antibodies were detected by ExtrAvidin peroxidase (Sigma). Undiluted peroxidase substrate 3,3,5,5-tetramethylbenzidine (TMB, Sigma) was incubated for 5 minutes at room temperature before the reaction was stopped by 1N HCl and read at 450 nm (BioTek Instruments, Winooska, Vt.). The assay was sensitive to 200 pg/ml.

Example 4

Specificity of Serum Amyloid P

Figure 4:
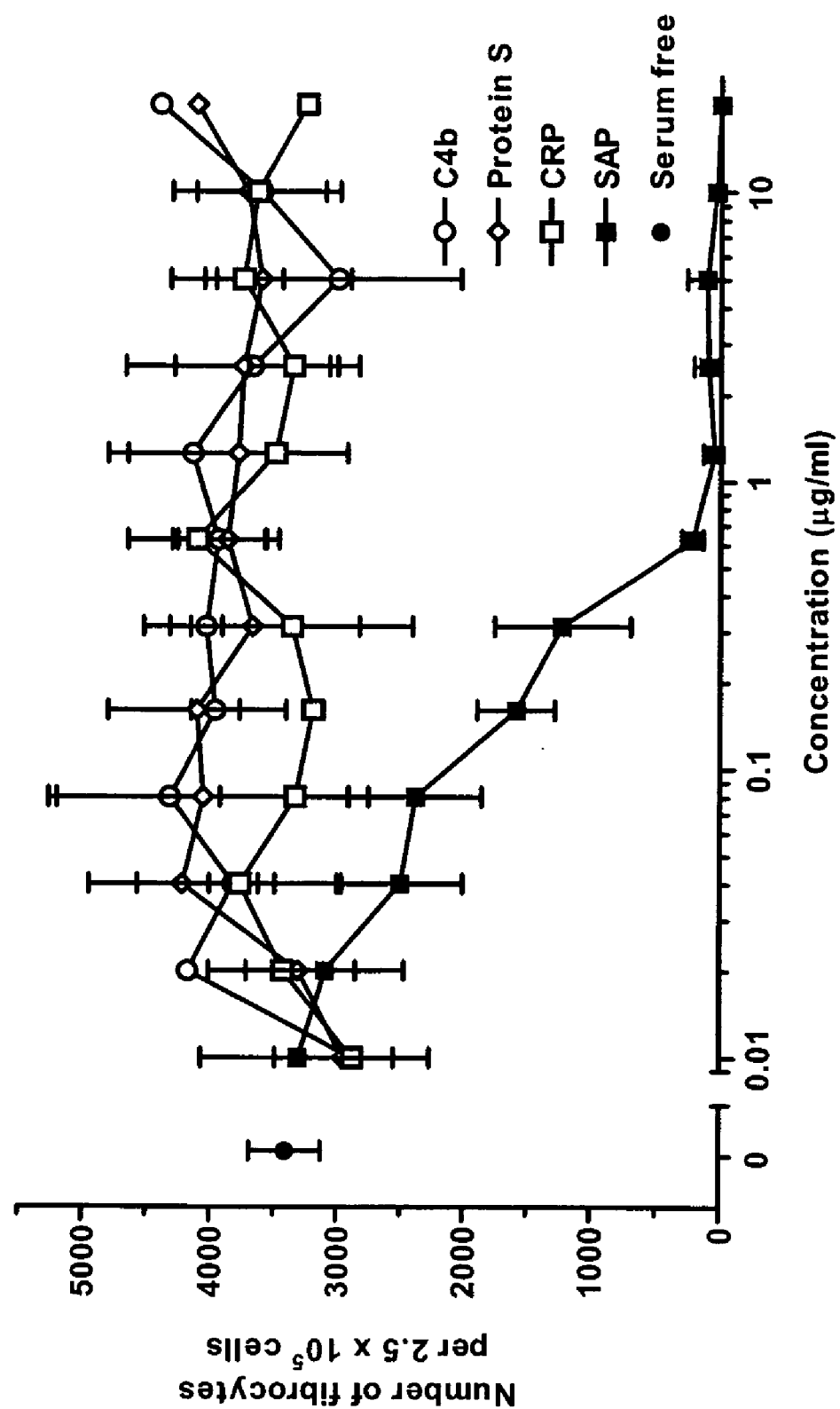
FIG. 4 shows the inhibition of fibrocyte formation by SAP, but not CRP or other plasma proteins. PBMC at 2.5×10$^5$ per ml were cultured in serum-free medium for 6 days in the presence of commercially available purified SAP (filled square), CRP (open square), Protein S (open diamond) or C4b (open circle) and then examined for the appearance of fibroblast-like cells. Cells were then air-dried, fixed, stained and fibrocytes enumerated by morphology. Results are mean±SD of fibrocytes per 2.5×10$^5$ PBMC (n=3 separate experiments).

Serum amyloid P is a constitutive plasma protein and is closely related to CRP, the major acute phase protein in humans. To assess whether other plasma proteins could also inhibit the differentiation of fibrocytes, PBMC were cultured in serum-free medium in the presence of commercially available purified SAP, CRP, C4b or Protein S. The commercially available SAP was purified using calcium-dependent affinity chromatography on unsubstituted agarose. Of the proteins tested, only SAP was able to inhibit fibrocyte differentiation, with maximal inhibitory activity at 1 µg/ml (FIG. 4). A dilution curve indicated that the commercially available SAP has approximately $6.6 \times 10^3$ units/mg of activity (FIG. 4). Serum and plasma contain between 30-50 µg/ml SAP. Fibrocytes began to appear at a plasma dilution of 0.5%, which would be approximately 0.15-0.25 µg/ml SAP, which is comparable to the threshold concentration of purified SAP. The data showing that SAP purified using two different procedures inhibits fibrocyte differentiation strongly suggests that SAP inhibits fibrocyte differentiation.

Figure 5A:
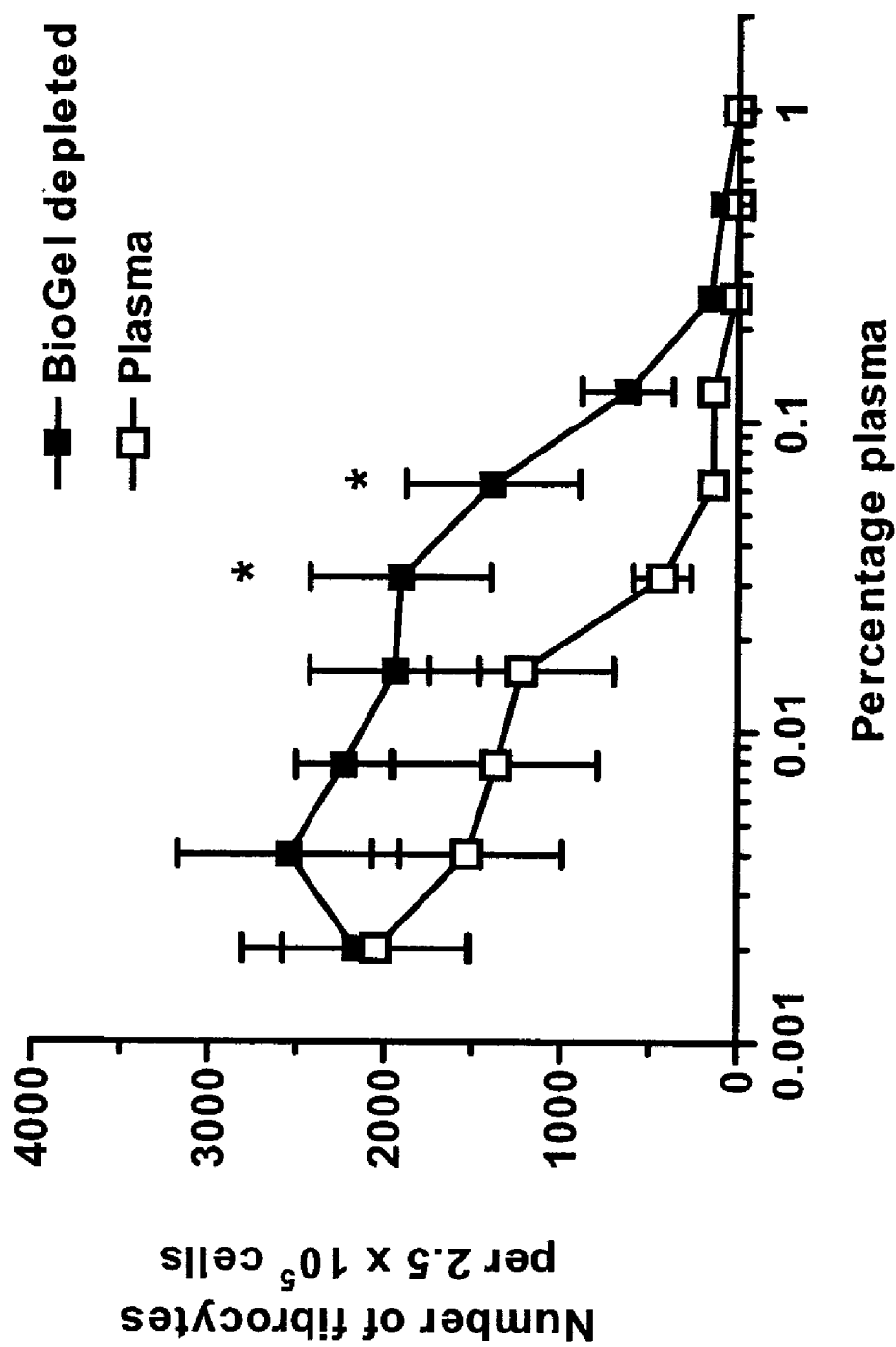
FIGS. 5A-5B show the effect of depletion of SAP from plasma in a fibrocyte differentiation assay.

Although these data indicate that SAP is capable of inhibiting fibrocyte development and SAP purifies in a manner that indicates that it is the active factor in plasma, it was not determined whether depletion of SAP from plasma and serum would negate the inhibition. Accordingly, SAP was depleted from plasma using agarose beads (BioGel A, BioRad). Plasma was diluted to 20% in 100 mM Tris pH 8, 150 mM NaCl, 5 mM $CaCl_2$ buffer and mixed with 1 ml agarose beads for 2 hours at 4° C. Beads were then removed by centrifugation and the process repeated. This depleted plasma was then assessed for its ability to inhibit fibrocyte differentiation. The control plasma diluted to 20% in 100 mM Tris pH 8, 150 mM NaCl, 5 mM $CaCl_2$ buffer had a similar dilution curve to that observed with untreated plasma. In contrast, the bead-treated plasma was less able to inhibit fibrocyte differentiation at intermediate levels of plasma. These data, along with the ability of purified SAP to inhibit fibrocyte differentiation, strongly suggest that SAP is the active factor in serum and plasma that inhibits fibrocyte differentiation. (See FIG. 5A).

Figure 5B:
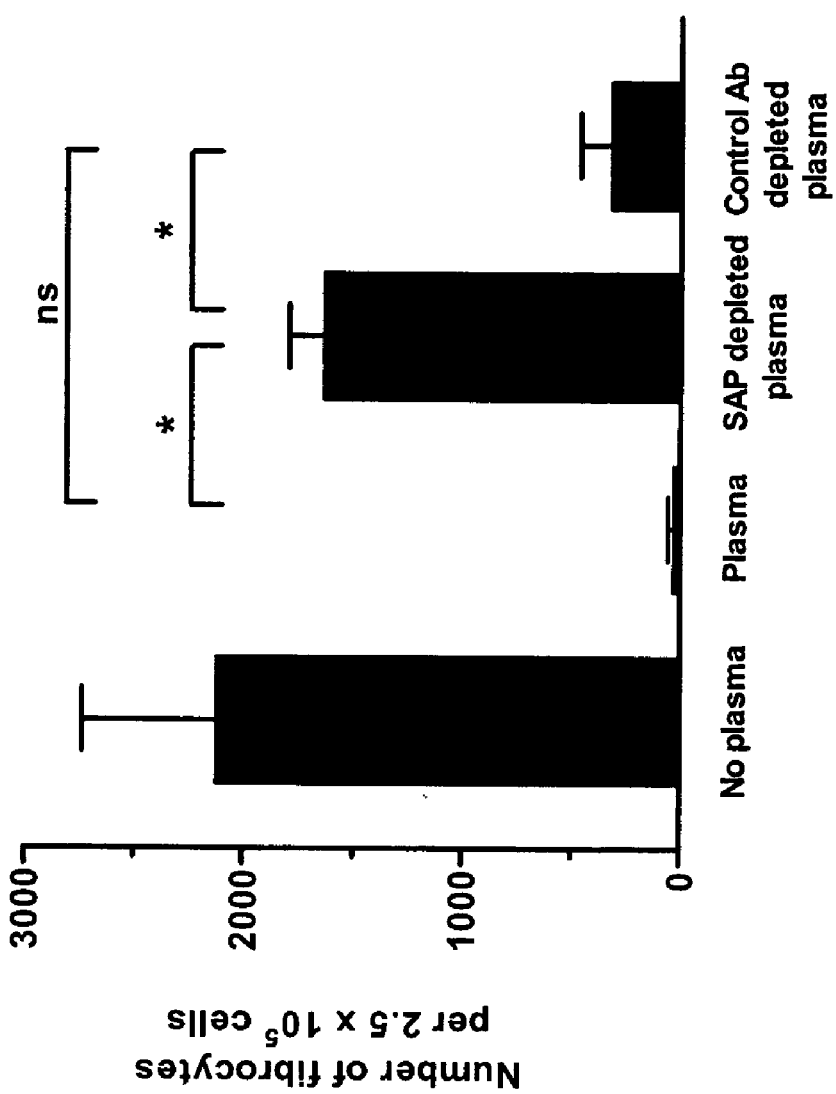

Plasma was also depleted of SAP using protein G beads coated with anti-SAP antibodies. Removal of SAP led to a significant reduction in the ability of plasma to inhibit fibrocyte differentiation compared with plasma, or plasma treated with beads coated with control antibodies ($p<0.05$) (FIG. 5B). The beads coated with control antibodies did remove some of the fibrocyte-inhibitory activity from plasma, but this was not significantly different from cells cultured with plasma. This probably reflects SAP binding to the agarose in the protein G beads. These data, together with the ability of purified SAP to inhibit fibrocyte differentiation, strongly suggest that SAP is the active factor in serum and plasma that inhibits fibrocyte differentiation.

Example 5

Antibodies and Proteins

Purified human CRP, serum amyloid P, protein S and C4b were purchased from Calbiochem (San Diego, Calif.). Monoclonal antibodies to CD1a, CD3, CD11a, CD11b, CD11c, CD14, CD16, CD19, CD34, CD40, Pan CD45, CD64, CD83, CD90, HLA-DR/DP/DQ, mouse IgM, mouse IgG1 and mouse IgG2a were from BD Pharmingen (BD Biosciences, San Diego, Calif.). Chemokine receptor antibodies were purchased from R and D Systems (Minneapolis, Minn.). Rabbit anti-collagen I was from Chemicon International (Temecula, Calif.), monoclonal C4b-binding protein was from Green Mountain Antibodies (Burlington, Vt.), sheep anti human C4b-binding protein was from The Binding Site (Birmingham, UK), monoclonal anti-CRP was from Sigma (St. Louis, Mo.). Polyclonal rabbit anti-protein S was from Biogenesis (Poole, Dorset, UK).

Example 6

Cell Separation

Peripheral blood mononuclear cells were isolated from buffy coats (Gulf Coast Regional Blood Center, Houston, Tex.) by Ficoll-Paque (Amersham Biosciences, Piscataway, N.J., USA) centrifugation for 40 minutes at 400×g. Depletion of specified leukocyte subsets was performed using negative selection using magnetic Dynabeads (Dynal Biotech Inc., Lake Success, N.Y.), as described previously. Briefly, PBMC were incubated with primary antibodies for 30 minutes at 4° C. Cells were then washed and incubated with Dynabeads coated with goat anti-mouse IgG for 30 minutes, before removal of antibody-coated cells by magnetic selection. This process was repeated twice. The negatively selected cells were routinely in excess of 98% pure as determined by monoclonal antibody labeling.

Example 7

Cell Culture and Fibrocyte Differentiation Assay

Cells were incubated in serum-free medium: RPMI (GibcoBRL Life, Invitrogen, Carlsbad, Calif., USA) supplemented with 10 mM HEPES (GibcoBRL/Life), 2 mM glutamine, 100 U/ml penicillin and 100 µg/ml streptomycin, 0.2% bovine serum albumin (BSA, Sigma), 5 µg/ml insulin (Sigma), 5 µg/ml iron-saturated transferrin (Sigma) and 5 ng/ml sodium selenite (Sigma). Normal human serum (Sigma), normal human plasma (Gulf Coast Regional Blood Center) or fetal calf serum (Sigma), column fractions, sera and synovial fluid from patients or purified proteins were added at the stated concentrations. Patient samples were obtained from a repository available to researchers at University of Texas Medical School at Houston. This repository keeps patient information confidential, and meets all NIH guidelines.

PBMC were cultured in 24 or 96 well tissue culture plates in 2 ml or 200 µl volumes respectively (Becton Dickinson, Franklin Lakes, N.J.) at 2.5×105 cells per ml in a humidified incubator containing 5% $CO_2$ at 37° C. for the indicated times. Fibrocytes in 5 different 900 µm diameter fields of view were enumerated by morphology in viable cultures as adherent cells with an elongated spindle-shaped morphology as distinct from small lymphocytes or adherent monocytes. Alternatively cells were air dried, fixed in methanol and stained with haematoxylin and eosin (Hema 3 Stain, VWR, Houston, Tex.). Fibrocytes were counted using the above criterion and the presence of an oval nucleus. Enumeration of fibrocytes was performed on cells cultured for 6 days in flat-bottomed 96 well plates, with 2.5×104 cells per well. In addition, fibrocyte identity was confirmed by immunoperoxidase staining (see below). The fibrocyte inhibitory activity of a sample was defined as the reciprocal of the dilution at which it inhibited fibrocyte differentiation by 50%, when added to serum-free medium.

Example 8

Purification and Characterization of Serum and Plasma Proteins 100 ml of frozen human serum or plasma was thawed rapidly at 37° C. and 1× "Complete" protease inhibitor (Roche, Indianapolis, Ind., USA), 1 mM benzamidine HCl (Sigma) and 1 mM Pefabloc (AEBSF: 4-(2-Aminoethyl)- benzenesulfonyl fluoride hydrochloride, Roche) were added. All subsequent steps were performed on ice or at 4° C. Barium citrate adsorption of plasma was performed as described previously. The precipitate was collected by centrifugation at 10,000×g for 15 minutes, resuspended in 20 ml of 100 mM $BaCl_2$ plus inhibitors and recentrifuged. After two rounds of washing, the pellet was resuspended to 20 ml in 10 mM sodium phosphate buffer pH 7.4 containing 5 mM EDTA and 1 mM benzamidine HCl and dialyzed for 24 hours against three changes of 4 liters of the same buffer.

Chromatography was performed using an Econo system (Bio-Rad, Hercules, Calif.) collecting 1 ml samples with a flow rate of 1 ml/min. The dialyzed barium citrate precipitate was loaded onto a 5 ml Hi-Trap Heparin column (Amersham Biosciences) and the column was washed extensively in 10 mM sodium phosphate buffer pH 7.4 until the absorbance at 280 nm returned to baseline. Bound material was eluted with a stepped gradient of 15 mls each of 100, 200, 300 and 500 mM NaCl in 10 mM sodium phosphate buffer pH 7.4. The fractions that inhibited monocyte to fibrocyte differentiation eluted at 200 mM NaCl. These were pooled (2 ml) and loaded onto a 5 ml Econo-Pak High Q column. After washing the column in 10 mM phosphate buffer, the bound material was eluted with the stepped gradient as above, with the active fraction eluting at 300 mM NaCl.

Active fractions from the High Q chromatography were concentrated to 200 µl using Aquacide II (Calbiochem) and then loaded onto a 4-20% native polyacrylamide gels (BMA, BioWhittaker, Rockland, Me.) as described previously. After electrophoresis, gel lanes were cut into 5 mm slices, mixed with 200 µl 20 mM sodium phosphate, 150 mM NaCl, 5 mM EDTA pH 7.4 containing 1 mM benzamidine HCl, crushed with a small pestle in an eppendorf tube and placed on an end-over-end mixer at 4° C. for 3 days. Proteins that eluted from the gel were analyzed for activity. To obtain amino acid sequences, proteins eluted from the gel slices were loaded onto a 4-20% gel with 100 µM thioglycolic acid in the upper chamber (Sigma). After electrophoresis the gel was rapidly stained with Coomasie brilliant blue, destained, and the bands excised off the gel. Amino acid sequencing was performed by Dr Richard Cook, Protein Sequencing Facility, Department of Immunology, Baylor College of Medicine.

Example 9

Western Blotting

For western blotting, plasma and serum samples were diluted 1:500 in 10 mM sodium phosphate pH 7.4. Fractions from heparin and High Q columns were not diluted. Samples were mixed with Laemmeli's sample buffer containing 20 mM DTT and heated to 100° C. for 5 minutes. Samples were loaded onto 4-20% Tris/glycine polyacrylamide gels (Cambrex). Samples for native gels were analyzed in the absence of DTT or SDS. Proteins were transferred to PVDF (Immobilon P, Millipore, Bedford, Mass.) membranes in Tris/glycine/SDS buffer containing 20% methanol. Filters were blocked with Tris buffered saline (TBS) pH 7.4 containing 5% BSA, 5% non-fat milk protein and 0.1% Tween 20 at 4° C. for 18 hours. Primary and biotinylated secondary antibodies were diluted in TBS pH 7.4 containing 5% BSA, 5% non-fat milk protein and 0.1% Tween 20 using pre-determined optimal dilutions (data not shown) for 60 minutes. ExtrAvidin-peroxidase (Sigma) diluted in TBS pH 7.4 containing 5% BSA and 0.1% Tween 20 was used to identify biotinylated antibody and chemiluminescence (ECL, Amersham Biosciences) was used to visualize the result.

Example 10

Immunohistochemistry

Cells cultured on 8 well glass microscope slides (Lab-Tek, Nalge Nunc International, Naperville, Ill.) were air dried before fixation in acetone for 15 minutes. Endogenous peroxidase was quenched for 15 minutes with 0.03% $H_2O_2$ and then non-specific binding was blocked by incubation in 2% BSA in PBS for 60 minutes. Slides were incubated with primary antibodies in PBS containing 2% BSA for 60 minutes. Isotype-matched irrelevant antibodies were used as controls. Slides were then washed in three changes of PBS over 15 minutes and incubated for 60 minutes with biotinylated goat anti-mouse Ig (BD Pharmingen). After washing, the biotinylated antibodies were detected by ExtrAvidin peroxidase (Sigma). Staining was developed with DAB (Diaminobenzadine, Sigma) for 3 minutes and counterstained for 30 seconds with Mayer's haemalum (Sigma).

Example 11

Expression of Surface Makers on Fibrocytes

PBMC were cultured in the wells of 8 well glass slides at 2.5×105 cells per ml (400 µl per well) in serum-free medium for 6 days. Cells were then air dried, fixed in acetone and stained by immunoperoxidase. Cells were scored positive or negative for the indicated antigens, compared to isotype-matched control antibodies.

Example 12

Recovery of Protein and Fibrocyte Inhibitory Activity from Fractionated Human Plasma Plasma was fractionated by $BaCl_2$ precipitation, heparin and ion exchange chromatography. Protein concentrations were assessed by spectrophotometry at 280 nm. Inhibition of fibrocyte differentiation was assessed by morphology. The fibrocyte inhibitory activity of a sample was defined as the reciprocal of the dilution at which it inhibited fibrocyte differentiation by 50%, when added to serum-free medium.

Example 13

Rat Wound Healing Studies Using High EEO Agarose Bandages

One application of the present invention relates to treatment of small wounds such as small cuts and surgical incisions as well as chronic ulcers, such as diabetic ulcers. Treatments developed for these and similar applications may also be readily modified for treatment of larger wounds and more serious problems.

Local depletion of SAP is important in wound healing and experiments such as those described above have revealed that SAP binds particularly well to a type of agarose known in the art as high EEO agarose. This binding has also been determined to be influenced by the presence of calcium.

Figure 6:
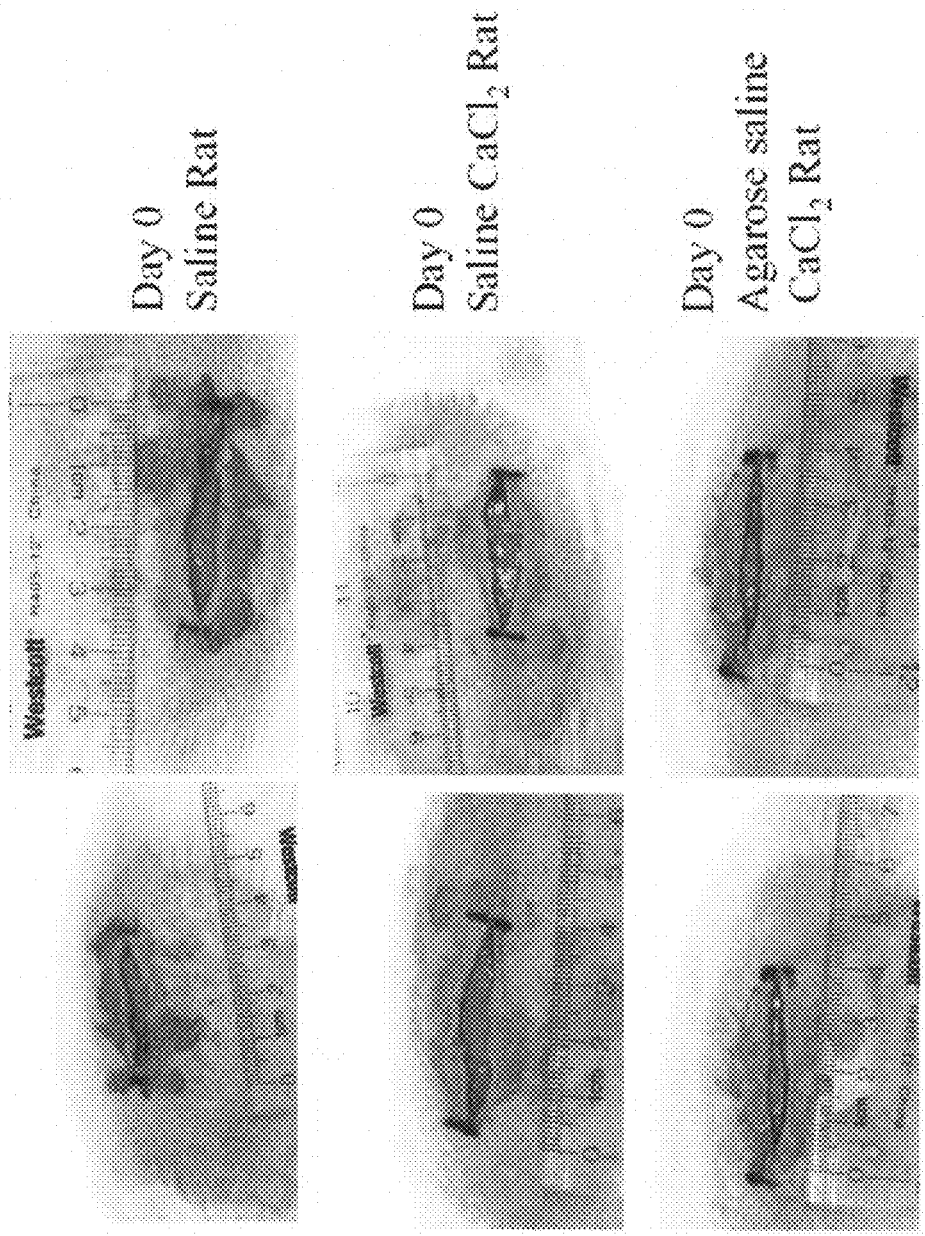
FIG. 6 shows initial skin incisions on three different rats to be treated with saline, saline with CaCl$_2$, or agarose with saline and CaCl$_2$.

To test the effects of a calcium/agarose bandage on wound healing, 4 cm wounds through the entire thickness of skin were made on the backs of three anesthetized rats. (See FIG. 6.) There was little bleeding from the wounds. One rat was treated only with a 4×4 gauze bandage (Topper 4×4 sponge gauze, Johnson & Johnson, Skillman, N.J.) lightly soaked with 1 ml saline solution (0.9% NaCl w/v in water). This layer of gauze was covered with a dry 4×4 gauze bandage, and these were held in place with several layers of Vetwrap® (3M Animal Care Products, St. Paul, Minn.) which were wrapped around the torso of the rat. A second rat was treated with a similar bandage, with the first layer lightly soaked (1 ml) with saline/5 mM $CaCl_2$.

A third rat was treated with an agarose/$CaCl_2$ bandage. To make the first layer of this bandage, 0.2 g of high EEO agarose (Electrophoresis grade high EEO Agarose product # BP-162, Fisher Scientific, Fair Lawn, N.J.) was dissolved in 20 ml of the saline/$CaCl_2$ solution described above by heating the solution in a 50 ml polypropylene tube (Falcon, Becton Dickinson, Franklin Lakes, N.J.) in a microwave oven until the mixture began to boil. After swirling to dissolve the agarose, 1 ml of the hot mixture was poured on a 4×4 gauze bandage that was laying flat on a piece of plastic wrap. The agarose-$CaCl_2$-saline impregnated gauze bandage was allowed to cool. This was then used as the first layer of the bandage for the third rat. A second layer of dry gauze and a cover of Vetwrap® were applied as in the first two rats.

Each rat was separately anesthetized, photographed, and bandaged to minimize differences in time between anesthetizing, wounding and bandaging.

Figure 8A:
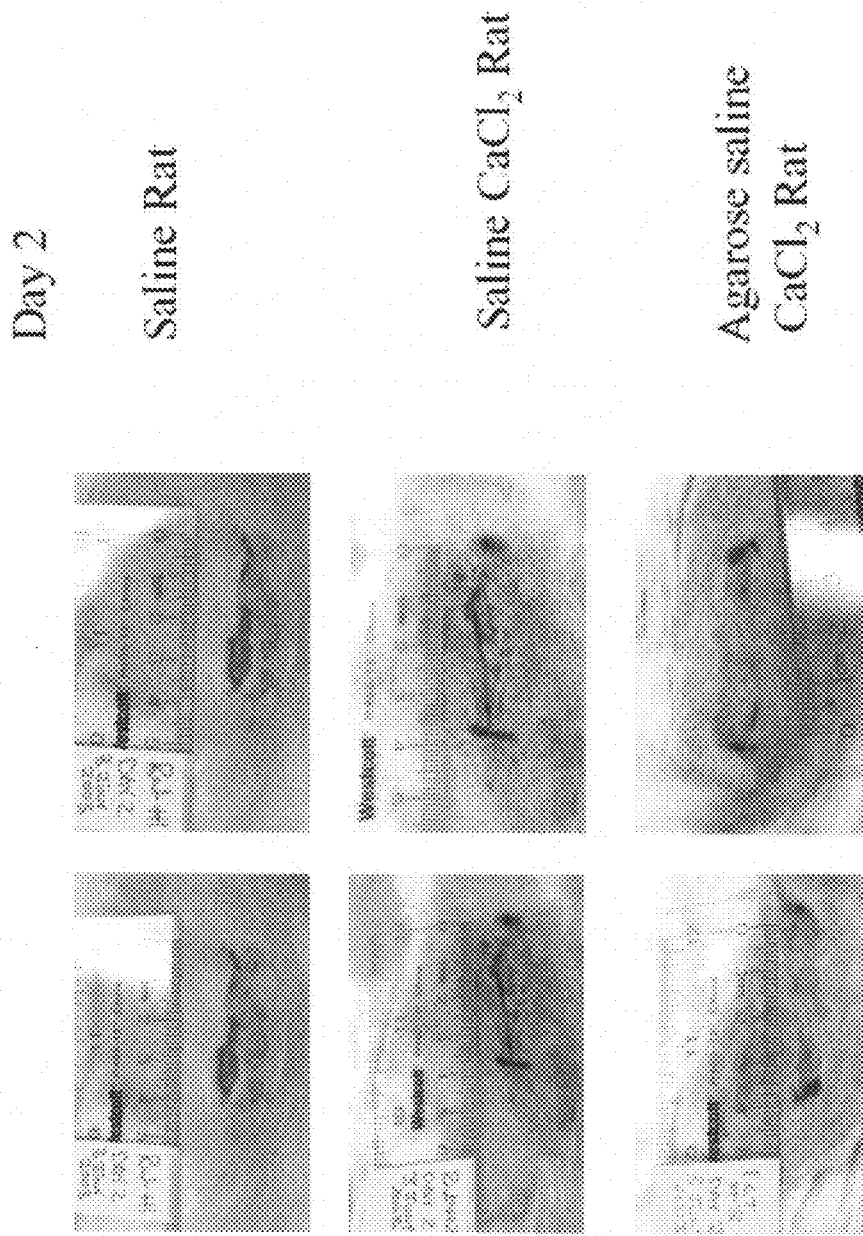
FIGS. 8A-8B also show healing of skin incisions on rats.
Figure 8B:
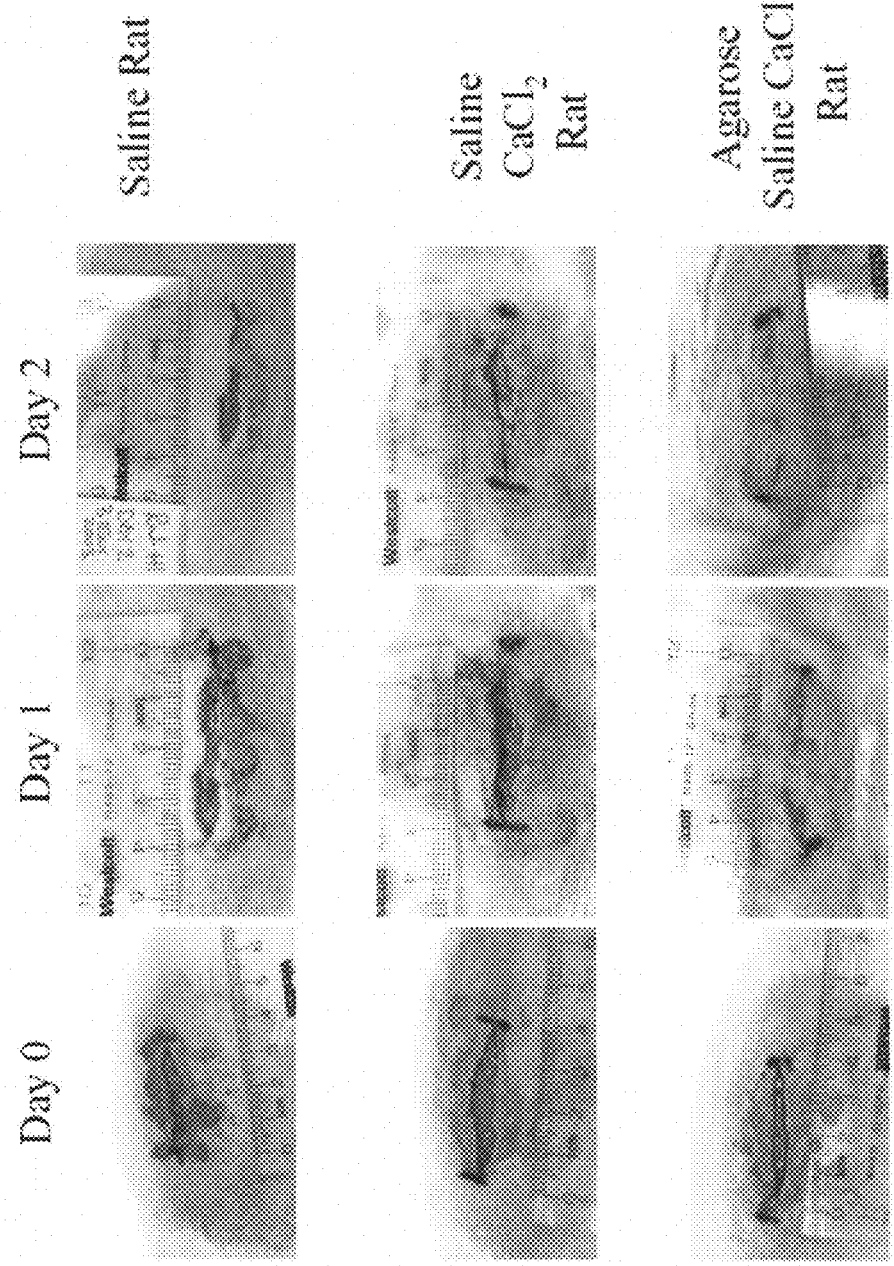

After 24 hours, the rats were lightly anesthetized and weighed, then the bandages were removed and the wounds were photographed. (See FIG. 7.) New bandages of the same initial composition were then reapplied to each of the rats. After another 24 hours this process was repeated to obtain additional pictures. (See FIG. 8.)

The rat treated with the agarose/$CaCl_2$ bandage showed considerably more rapid wound healing than either of the other two rats. (See FIG. 8B.)

Although an agarose bandage was reapplied each day in the present example, in other embodiments of the invention an agarose bandage may be applied only initially or initially and on the first day or so followed by a dry bandage once the wound has substantially closed. Once the wound has closed, the ability of agarose to absorb SAP may be limited. Wounds that have closed may also benefit from a dryer environment.

Although hydrated agarose was used in the present example, it may be possible to also utilize bandages and other formulations with less hydrated agarose. The agarose may be wetted by serum escaping from the wound itself.

Topical agarose preparations of the present invention may also be prepared using antiseptics to allow both cleansing of the wound and promotion of wound healing. In a specific example, the agarose may be prepared with alcohol, which may cleanse the wound initially then evaporate over time.

Example 14

Additional Factors for Use in Topical Wound Healing Embodiments

Although the above agarose bandages proved quite effective in promoting wound healing, the observed effects can most likely be improved by the addition of other wound healing factors to the bandages or other topical agarose formulations. Such factors may include any compound or compositions, such as small molecules or polypeptides.

In particular, these factors may influence a separate wound healing pathway, or they may influence the fibrocyte formation pathway. They may also influence the fibrocyte formation pathway in a different manner than SAP, or they may influence it by a mechanism similar to that of SAP, for example antibodies in the agarose formulation may bind and inactivate additional SAP.

Factors may also be included that address other problems, some of which may also affect wound healing. For example, agarose bandages for hemophiliac patients may additionally include clotting factors to help stop or prevent bleeding from the wound.

In a particular embodiment, IL-4 and/or IL-13 may be included in the agarose formulation. Both are potent activators of the fibrotic response. IL-4 has been previously described to play a role in wound repair and healing.

Figure 9:
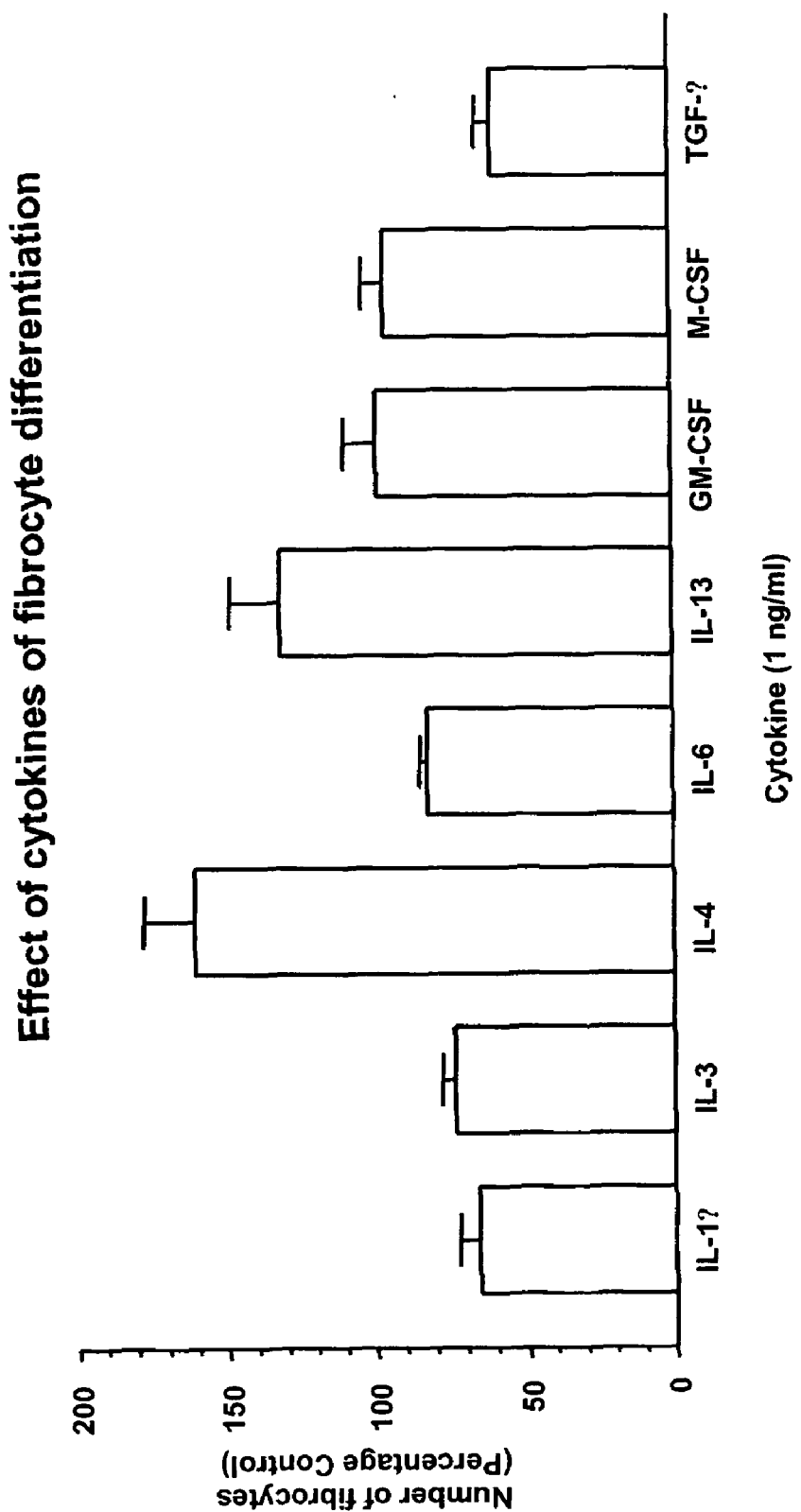
FIG. 9 shows the effects of various cytokines on promotion of fibrocyte differentiation.

Experiments have shown that IL-4 and IL-13 are capable of promoting fibrocyte differentiation in vitro. Specifically, PBMC were cultured in serum-free medium in the presence of IL-4 or IL-13. Concentrations of either IL-4 or IL-13 between 10 and 0.1 ng/ml enhanced the number of fibrocytes in culture. (See FIG. 9.) This indicates that IL-4 and IL-13 are capable of promoting the differentiation of fibrocyte precursors into mature fibrocytes. Therefore a bandage or other topical agarose formulation as described above additionally containing IL-4 and/or IL-13 is expected to show further improvements in wound healing.

Other factors that may be added to agarose bandages or topical formulations as described above or physiological conditions to be mimicked include:
Molecules known to bind to SAP:
Collagen IV;
Laminin;
Fibronectin;
C4BP;
Aggregated Fc of IgG;
CD16, CD32 and CD64: Fc Receptors;
Heparin;
LPS;
Apoptotic cells, especially chromatin and DNA
Zymozan.
Physiological conditions related to SAP binding:
SAP exhibits calcium-dependent binding to amyloid fibers formed from, e.g. serum amyloid A (SAA), immunoglobulin light chains, β2 microglobulin, transthyretin and the neurofibrillary tangles;
SAP binds to surfaces of bacteria due to expression of pyruvate acetyl of galactose and to other sugars on the surface of bacteria.
SAP binds to the "artificial" ligands on high EEO agarose and phosphoethanolamine-agarose, and with low affinity to phosphocholine-sepharose. These features give rise to two ways of purifying SAP from serum or plasma. First, SAP may be bound to high EEO agarose via the pyruvate acetyl of galactose, which is a minor constituent of agarose preparations. Second, SAP may be bound to phosphoethanolamine-agarose, which is presently the preferred method of SAP purification in the art. Thus, phosphoethanolamine-agarose may be used for bandages or topical formulations.

Example 15

Methods of Identifying Suitable SAP-Binding Agents Including Derivatized Agarose Because the biological function of SAP includes opsonization of foreign molecules for enhanced uptake by macrophages, other derivitized agaroses incorporating motifs such as bacterial cell wall carbohydrates, DNA or DNA analogs, and the like may also be used if they meet the following criterion for activity.

Prepare a 100 microliter sample of SAP at 20 micrograms/milliliter. Add insoluble adsorbent in an amount that increases the volume of the sample by less than 100%. Incubate with gentle shaking or end over end rotation for 1 hour. Centrifuge to pellet the adsorbent. Measure remaining SAP in the supernatant. If more than 50% of the SAP has been removed, the adsorbent is deemed active.

The methodology may also be used to identify and test other SAP-binding agents.

Example 16

Pig Wound Healing Studies Using Agarose Hydrogels

The effects of agarose hydrogels on deep partial thickness wound healing in a porcine model were also studied. The porcine model has morphological similarities to human skin. A total of seven young female specific pathogen free (SPF: Ken-O-Kaw Farms, Windsor, Ill.) pigs weighing 25-30 kg were maintained in constant conditions for two weeks prior to the experiment. These animals were fed a basal diet ad libitum and were housed individually in animal facilities in compliance with the American Association for Accreditation of Laboratory Animal Care with controlled temperature (19-21° C.) and lighting (12 hours light/12 hours dark).

The flank and back of the experimental animals were clipped with standard animal clippers on the day of the experiment. The skin on both sides of each animal was prepared for wounding by washing with a non-antibiotic soap (Neutrogena Soap Bar; Johnson & Johnson, Calif.) and sterile water. Each animal was anesthetized intramuscularly with tiletamine HCl plus zolazepam (1.4 mg/kg) (Telazol; Laderle Patenterals Inc., Puerto Rico), xylazine (2.0 mg/kg) (X-jet; Phoenix Scientific Inc., MO), and atropine (0.04 mg/kg) (Atrojet SA, Phoenix Scientific Inc., MO) followed by mask inhalation of isoflurane (Isothesia, Abbott Laboratories, IL) and oxygen combination.

One hundred and sixty (160) rectangular wounds measuring 10 mm×7 mm×0.5 mm were made in the paravertebral and thoracic area with a specialized electrokeratome fitted with a 7 mm blade. The wounds were separated from one another by 15 mm of unwounded skin.

Forty wounds were randomly assigned to a treatment group according to one the three experimental designs. One animal in a preliminary study was assigned to a treatment group where wounds received either i) ME Agarose gel, ii) SP Agarose gel, ii) the vehicle alone, or iv) were untreated and exposed to air. Both ME Agarose ans SP Agarose gels met the criteria stated in Example 15.

One other animal in the preliminary study was assigned to a treatment group where wounds received either i) SP Agarose gel, ii) the vehicle alone, iii) Vigilon wound dressing (C.R. Bard, Inc., GA) or iv) were untreated and exposed to air.

For the preliminary study, three animals were included. In these experiments two hydrogel test agents (SP and ME Agarose) along with positive and negative controls were evaluated. These treatments were randomized among these three animals with two of the animals receiving SP Agarose hydrogel material. Because it appeared that the SP material was more effective than the ME Agarose hydrogel, four additional animals were studied using the SP Agarose hydrogel alone.

Four animals were assigned to a treatment group where wounds received either i) SP Agarose gel, ii) the vehicle alone, iii) Vigilon, or iv) were untreated and exposed to air. All wounds in all treatment groups were covered with a polyurethane dressing except those that were untreated an exposed to air.

Figure 10:
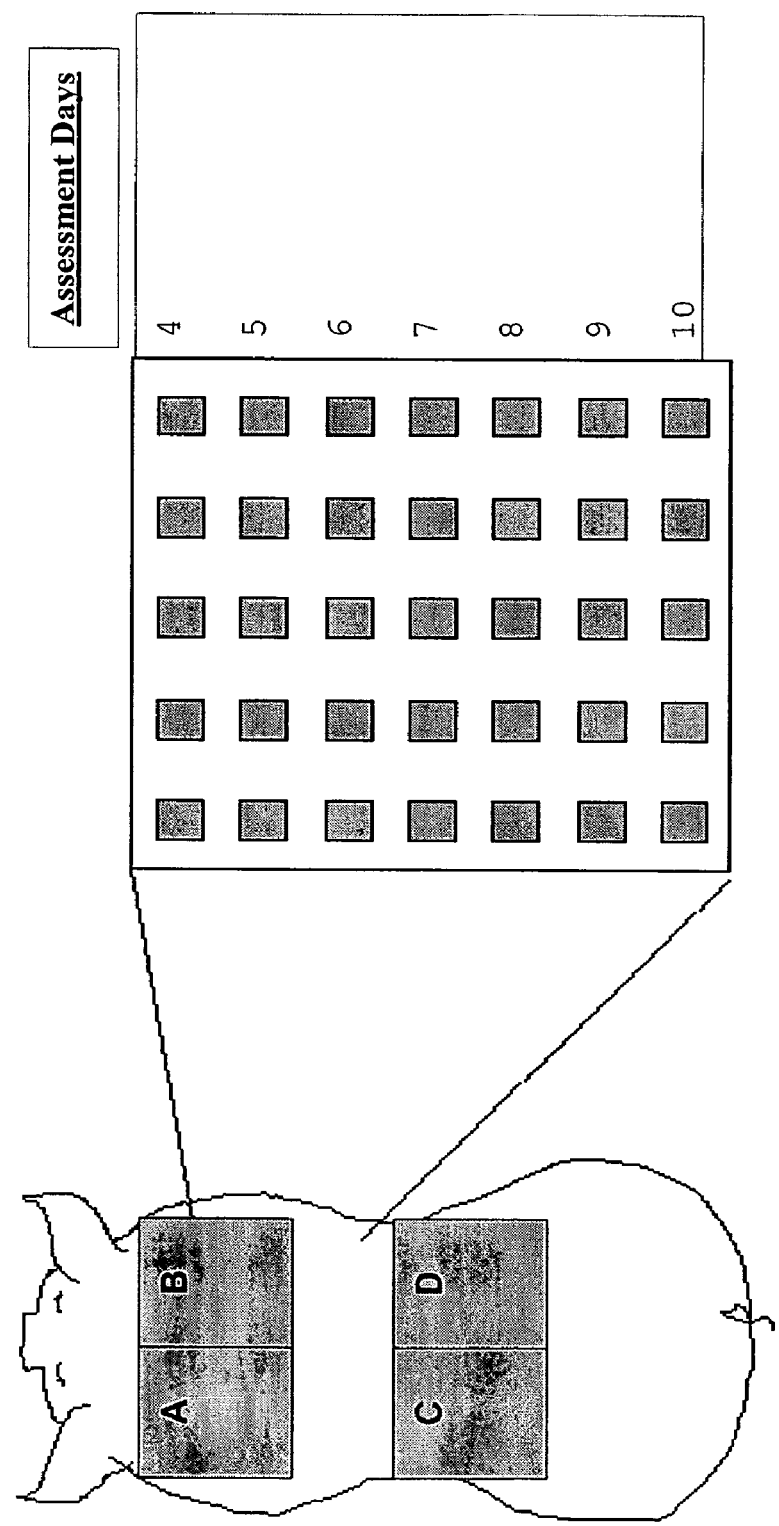
FIG. 10 shows an experimental setup in a porcine model.

The application and assessment of different treatment groups is shown in FIG. 10. Areas A, B, C, and D are repeated areas of treatment.

All hydrogel treated wounds were treated by placing the hydrogel mateial over the wounds and surrounding normal skin to the approximate thickness of the Vigilon (~1 mm). The hydrogel was then covered with a polyurethane dressing to prevent desiccation. One day 1 after treatment, the animals were anesthetized and the dressings observed to make sure they were still intact. All materials were kept in place until wound evaluation unless it was observed that the materials needed to be replaced. In order to assess the wounds, a portion of the hydrogel was removed to uncover five wounds for evaluation. Wounds were evaluated for epithelization as described below.

Animals were monitored daily for any observable signs of pain or discomfort. In order to help minimize possible discomfort, an analgesic buprenorphine 0.03 mg/kg (Buprenex injectable, Reckitt Benckiser Hull, England) was given to each animal on the first day, and every third day thereafter, while under anesthesia. A fentanyl transdermal system: 25 µg/hr (Duragesic; Alza Corp., CA) was used during the entire experiment.

Wounds were examined regularly for any signs of erythema (redness) and infection. The physical characteristics of the material were also noted.

Figure 11:
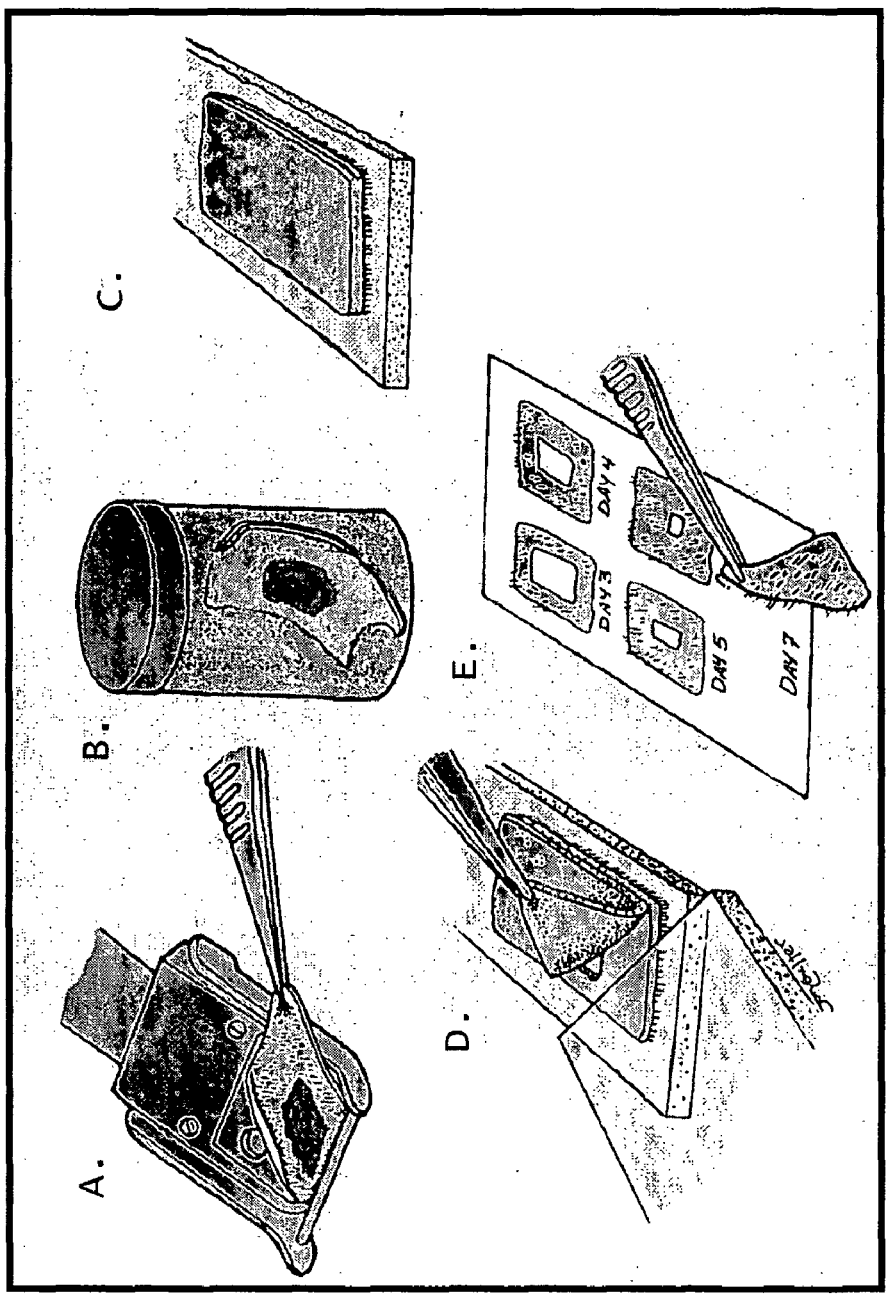
FIG. 11 shows the steps of an epidermal migration assessment in a porcine model. A: wound excision; B: placement of specimen in sodium bromide for incubation; C: placement of specimen on glass slide for separation; D: separation of specimen; D: placement of epidermal specimen on cardboard for permanent record.

Beginning on day 3 after wounding for the first 3 pigs in the preliminary study and on day 4 after wounding for the final 4 pigs and on each day thereafter until the time of healing (day 6 for most treatment groups), five wounds and the surrounding normal skin from each treatment group were excided using an electrokeratome with a 22 mm blade set to a depth of 0.7 mm. (See FIG. 10.) All specimens that were not excised intact were discarded. The excised skin containing the wound site was inclubated in 0.5 M sodium bromide at 37° C. for 24 hours, allowing for a separation of the dermis from the epidermis. After separation, the epidermal sheet was examined macroscopically for defects. (FIG. 11.) Defects were defined as holes in the epidermal sheet or as a lack of epidermal continuity in the area of the wound. Epithelization was considered complete (healed) if no defect(s) were present; any defect in the wound area indicates that healing is incomplete.

The hydrogel materials did not cause any re-injury of wounds during removal throughout the entire assessment time. During the later evaluations (days 8-10) the hydrogel materials appeared to decrease in thickness (density) and became moderately desiccated, forming a glue-like substance.

The untreated air exposed wounds displayed prominent crust formation as compared to wounds from the other treatment groups. None of the wounds from any of the treatment groups showed signs of erythema or infection. Wounds treated with all hydrogel materials appeared to have significantly less crust formation as compared to wounds in the untreated air exposed group.

Figure 12:
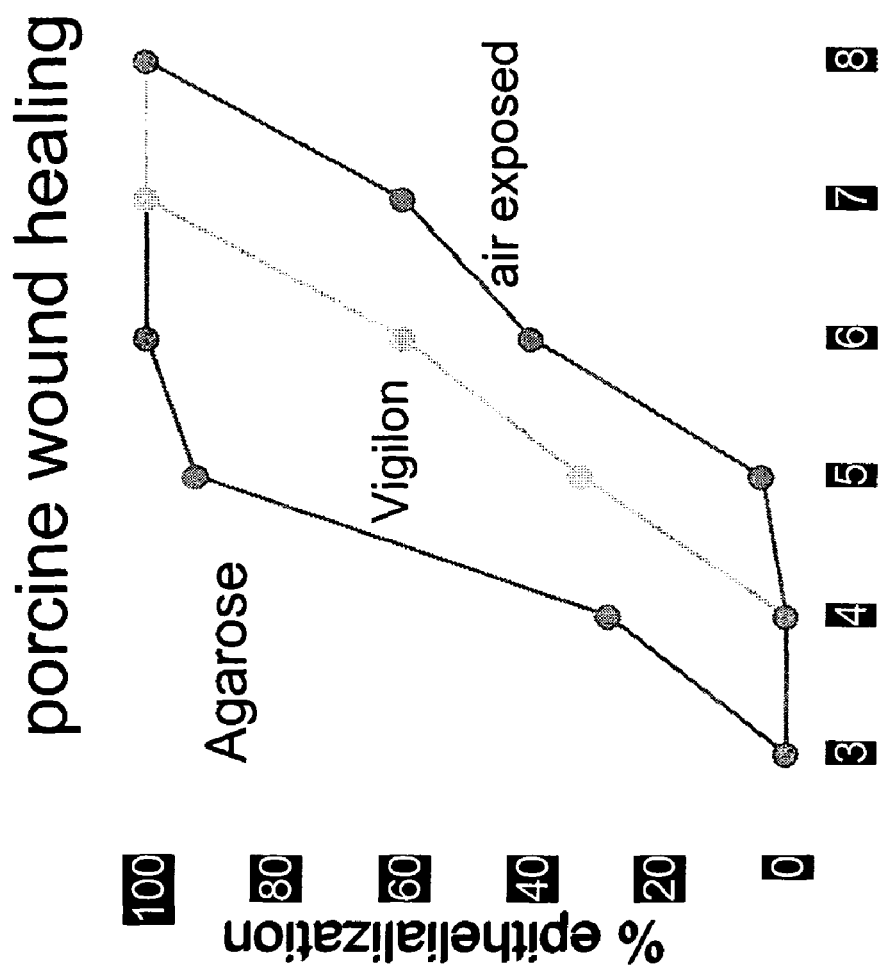
FIG. 12 shows the combined healing data from porcine wound healing studies. Day after wounding is indicated on the x axis.

After the study was completed the number of wounds completely healed (completely epithelized) was divided by the total number of wounds sampled per day and multiplied by 100 to detrmine the % epilthelization (FIG. 12).

The Chi square test was used to determine statistical significance between the treatment groups. All data show in FIG. 12 varied in a statistically significant manner based on this test.

Specific results by day were also examined. On day 3 none of the wounds in any treatment group were healed.

On day 4, 33% of the wounds treated with the SP Agarose hydrogel were healed. 13% of the wounds treated with the vehicle were healed. None of the other wounds were healed on that day.

On day 5, 90% of the wounds treated with SP Agarose gel were completely re-epithelized and 80% of the wounds in the vehicle group were healed. Wounds in the Vigilon group were 56% healed and 3% of the wounds in the untreated group were healed.

On day 6, 100% of the wounds treated with SP Agarose gel, Vigilon and the vehicle were healed. Only 40% of the untreated wounds were healed.

On day 7, 100% of the wounds from all treatment groups were completely re-epithelized except those from the untreated group, which were 60% healed.

On day 8, all wounds from each treatment group were completely re-epithelized.

These results collectively show that all hydrogel treatment groups increased the rate of epithelization as compared to untreated, air-exposed control wounds. These treatment groups initiated 100% complete epithelization two days earlier than the untreated, air-exposed wounds.

Further, wounds treated with the SP Agarose hydrogel healed significantly faster than wounds treated with Vigilon.

Although only exemplary embodiments of the invention are specifically described above, it will be appreciated that modifications and variations of these examples are possible without departing from the spirit and intended scope of the invention.

The invention claimed is:

1. A wound dressing comprising:
a Serum Amyloid P (SAP)-binding agarose, the SAP-binding agarose operable to promote healing of a skin injury or laceration in a mammal; and
  a divalent cation in an amount sufficient to promote healing of the skin injury or laceration in conjunction with the SAP-binding agarose in a concentration sufficient to promote healing of the skin injury or laceration more quickly than the SAP-binding agarose alone.

2. The wound dressing of claim 1, further comprising an additional wound healing factor.

3. The wound dressing of claim 2, wherein the additional wound healing factor is selected from the group consisting of: interleukin (IL)-4, IL-13, fibroblast growth factor (FGF), transforming growth factor beta (TGFβ), and any combinations thereof.

4. The wound dressing of claim 1, further comprising IL-13 at a concentration of 0.1 to 10 ng/ml.

5. The wound dressing of claim 1, further comprising IL-4 at a concentration of 0.1 to 10 ng/ml.

6. The wound dressing of claim 1, further comprising a bandage.

7. The wound dressing of claim 1, wherein the divalent cation is $Ca^{2+}$.

8. A wound dressing comprising:
a Serum Amyloid P (SAP)-binding high electroendosmosis (EEO) agarose, the SAP-binding agarose operable to promote healing of a skin injury or laceration in a mammal; and
a divalent cation in an amount sufficient to promote healing of the skin injury or laceration in conjunction with the SAP-binding agarose in a concentration sufficient to promote healing of the skin injury or laceration more quickly than the SAP-binding agarose alone.

9. The wound dressing of claim 8, wherein the divalent cation is $Ca^{2+}$.

10. The wound dressing of claim 9, further comprising approximately 1% (w/v) high EEO agarose.

11. The wound dressing of claim 8, further comprising an additional wound healing factor.

12. The wound dressing of claim 11, wherein the additional wound healing factor is selected from the group consisting of: interleukin (IL)-4, IL-13, fibroblast growth factor (FGF), transforming growth factor beta (TGFβ), and any combinations thereof.

13. The wound dressing of claim 12, further comprising IL-13 at a concentration of 0.1 to 10 ng/ml.

14. The wound dressing of 12, further comprising IL-4 at a concentration of 0.1 to 10 ng/ml.

15. The wound dressing of claim 8, further comprising a bandage.

16. The wound dressing of claim 8, wherein the SAP-binding high EEO agarose comprises a pyruvate acetal of galactose.

17. A wound dressing comprising:
a Serum Amyloid P (SAP)-binding agarose comprising a phosphoethanolamine moiety, the SAP-binding agarose operable to promote healing of a skin injury or laceration in a mammal; and
a divalent cation in an amount sufficient to promote healing of the skin injury or laceration in conjunction with the SAP-binding agarose in a concentration sufficient to promote healing of the skin injury or laceration more quickly than the SAP-binding agarose alone.

18. The wound dressing of claim 17, wherein the divalent cation is $Ca^{2+}$.

19. The wound dressing of claim 17, further comprising an additional wound healing factor.

20. The wound dressing of claim 19, wherein the additional wound healing factor is selected from the group consisting of: interleukin (IL)-4, IL-13, fibroblast growth factor (FGF), transforming growth factor beta (TGFβ), and any combinations thereof.

21. The wound dressing of claim 17, further comprising IL-13 at a concentration of 0.1 to 10 ng/ml.

22. The wound dressing of claim 17, further comprising IL-4 at a concentration of 0.1 to 10 ng/ml.

23. The wound dressing of claim 17, further comprising a bandage.

\* \* \* \* \*